US009248171B2

(12) United States Patent
Saint-Remy

(10) Patent No.: US 9,248,171 B2
(45) Date of Patent: Feb. 2, 2016

(54) IMMUNOGENIC PEPTIDES AND THEIR USE IN TRANSPLANTATION

(75) Inventor: Jean-Marie Saint-Remy, Grez-Dolceau (BE)

(73) Assignee: IMCYSE SA, Sart-Tilman (BE)

( * ) Notice: Subject to any disclaimer, the term of this patent is extended or adjusted under 35 U.S.C. 154(b) by 367 days.

(21) Appl. No.: 12/735,744

(22) PCT Filed: Feb. 14, 2008

(86) PCT No.: PCT/BE2008/000010
§ 371 (c)(1),
(2), (4) Date: Aug. 13, 2010

(87) PCT Pub. No.: WO2009/100505
PCT Pub. Date: Aug. 20, 2009

(65) Prior Publication Data
US 2011/0110964 A1    May 12, 2011

(51) Int. Cl.
*A61K 39/00*      (2006.01)
*A61K 38/00*      (2006.01)
*A61K 38/03*      (2006.01)
*C07K 14/74*      (2006.01)
*C12N 9/02*       (2006.01)

(52) U.S. Cl.
CPC ............... *A61K 39/001* (2013.01); *A61K 38/03* (2013.01); *C07K 14/70539* (2013.01); *C12N 9/0036* (2013.01); *C07K 2319/00* (2013.01); *C07K 2319/06* (2013.01)

(58) Field of Classification Search
None
See application file for complete search history.

(56) References Cited

U.S. PATENT DOCUMENTS

| | | | |
|---|---|---|---|
| 4,886,782 A | 12/1989 | Good et al. | |
| 5,863,528 A | 1/1999 | Hawley et al. | |
| 6,759,046 B1 | 7/2004 | Gaudernack et al. | |
| 7,157,089 B1 | 1/2007 | Mizzen et al. | |
| 2003/0049723 A1 | 3/2003 | Zhang et al. | |
| 2003/0104570 A1 | 6/2003 | Cabezon Silva et al. | |
| 2003/0129205 A1 | 7/2003 | Saint-Remy et al. | |
| 2004/0077045 A1 | 4/2004 | Zhang et al. | |
| 2005/0196386 A1 | 9/2005 | Blazar et al. | |
| 2005/0202044 A1 | 9/2005 | Mizzen et al. | |
| 2006/0211091 A1 | 9/2006 | Zhang et al. | |
| 2006/0269561 A1 | 11/2006 | Paterson et al. | |
| 2007/0160620 A1 | 7/2007 | Mizzen et al. | |
| 2010/0330088 A1 | 12/2010 | Saint-Remy | |
| 2011/0002903 A1 | 1/2011 | Saint-Remy | |
| 2011/0111502 A1 | 5/2011 | Saint-Remy | |
| 2012/0009678 A1 | 1/2012 | Saint-Remy | |
| 2013/0095133 A1* | 4/2013 | Klatzmann et al. | 424/192.1 |

FOREIGN PATENT DOCUMENTS

| | | |
|---|---|---|
| WO | WO 99/58552 | 11/1999 |
| WO | WO 01/70263 | 9/2001 |
| WO | WO 02/00892 | 1/2002 |
| WO | WO 02/095051 | 11/2002 |
| WO | WO 2005/039613 | 5/2005 |
| WO | WO 2007/104715 | 9/2007 |
| WO | WO 2008/017517 | 2/2008 |
| WO | WO 2009/100505 | 8/2009 |
| WO | WO 2009/101204 | 8/2009 |
| WO | WO 2009/101205 | 8/2009 |
| WO | WO 2009/101206 | 8/2009 |
| WO | WO 2009/101207 | 8/2009 |
| WO | WO 2009/101208 | 8/2009 |

OTHER PUBLICATIONS

Oliveira et al., 2010, Biochem vol. 49: 3317-26.*
Wobus et al., 2005, Physiol Rev. vol. 85: 635-678.*
Batten et al., 2007, Phil. Trans. R. Soc. vol. 362: 1343-56.*
Li et al., 2009, World J. Stem Cells, vol. 1: 30-35.*
Toyokawa et al., 2008, Liver Transpl. vol. 14: 346-57.*
Boisgerault et al., 2009, Transplantation, vol. 87: 16-23.*
Tindle et al., 1991, PNAS vol. 88: 5887-91.*
Reznik et al., 2001, Am. J. Transpl. vol. 1: 228-235.*
European Patent Office, Communication dated Apr. 5, 2013, issued by Herald Schmidt, in connection with European Patent Application No. 08 706 161.0.
International Search Report for PCT/BE2008/000010, mailed Jul. 2, 2008.
Written Opinion of the International Searching Authority for PCT/BE2008/000010, mailed Jul. 2, 2008.
Aleksza, M. et al., "Altered cytokine expression of peripheral blood lymphocytes in polymyositis and dermatomyositis", Ann. Rheum. Dis., vol. 64, (2005), pp. 1485-1489.
Bolivar, J. et al, "Molecular cloning of a zinc finger autoantigen transiently associated with interphase nucleolus and mitotic centromeres and midbodies. Orthologous proteins with nine CXXC motifs highly conserved form nematodes to humans", J. Biol, Chem., vol. 274, (1999), pp. 36456-36464.
Braun, M.Y. et al., "Acute rejection in the absence of cognate recognition of allograft by T cells", J. Immunol., vol. 166, No. 8, (2001), pp. 4879-4883.
Brinster, C. et al., "Costimulatory effects of IL-1 on the expansion/differentiation of CD4+CD25+Foxp3+ and CD4+CD25+Foxp3− T cells", J. Leukoc. Biol., vol. 84, (2008), pp. 480-487.

(Continued)

*Primary Examiner* — Amy Juedes

(74) *Attorney, Agent, or Firm* — Nixon & Vanderhye, P.C.

(57) ABSTRACT

The present invention relates to the use of immunogenic peptides comprising a T-cell epitope derived from an allograft antigen and a redox motif such as C-(X)2-[CST] or [CST]-(X)2-C in the prevention and/or treatment of allograft rejection and in the manufacture of medicaments therefore.

15 Claims, No Drawings

(56) References Cited

OTHER PUBLICATIONS

Cao, O. et al, Prevention of gene transfer-induced inhibitor formation by nasal administration of human F.IX T cell epitope in a murine model of hemophilia B., Blood, vol. 104, (2004), pp. 121A-122A.
Chen, T. C. et al., Induction of dominant transplantation tolerance by an altered peptide ligand of the male antigen Dby., .J Clin. Invest., vol. 113, No. 12, (2004), pp. 1754-1762.
Davids, B.J. et al., A new family of giardial cysteine-rich non-VSP protein genes and a novel cyst protein, PLOS. ONE., vol. 1, (2006), e44.
De La Cruz, V.F. et al., "The immunologic significance of variation within malaria circumsporozoite protein sequences", J. Immunol., vol. 142, (1989), pp. 3568-3575.
Eberl, G. et al., "Tissue-specific segregation of CD1d-dependent and CD1d-independent NK T cells", J. Immunol., vol. 162, (1999), pp. 6410-6419.
Dobrzynski, E. et al, "Prevention of cytotoxic T lymphocyte responses to factor IX-expressing hepatocytes by gene transfer-induced regulatory T cells", Proc. Natl. Acad Sci. U.S.A., vol. 103, (2006), pp. 4592-4597.
Fomenko, D.E. et al., "Identity and functions of CxxC-derived motifs", Biochemistry, vol. 42, (2003), pp. 11214-11225.
Geluk, A. et al., "HLA-DR binding analysis of peptides from islet antigens in IDDM", Diabetes, vol. 47, (1998), pp. 1594-1601.
Gross, D.A. et al., "Simple conditioning with monospecific CD4+CD25+ regulatory T cells for bone marrow engraftment and tolerance to multiple gene products", Blood, vol. 108, No. 6, (2006), pp. 1841-1848.
Grossman, W.J., et al, "Differential expression of granzymes A and B in human cytotoxic lymphocyte subsets and T regulatory cells", Blood, vol. 104, (2004), pp. 2840-2848.
Hohn, H. et al., "CD4+ tumor-infiltrating lymphocytes in cervical cancer recognize HLA-DR-restricted peptides provided by human papillomavirus-E7", J. Immunol., vol. 163, (1999), pp. 5715-5722.
Hori, S. et al., "Control of regulatory T cell development by the transcription factor Foxp3", Science, vol. 299, (2003), pp. 1057-1061.
Ise, W. et al., "Naïve CD4+ T cells exhibit distinct expression patterns in cytokines and cell surface molecules on their primary responses to varying doses of antigen", J. Immunol., vol. 168, (2002), pp. 3242-3250.
James, E. et al., HY peptides modulate transplantation responses to skin allografts, Int. Immunol., vol. 14, No. 11, (2002), pp. 1333-1342.
Joffre, O. et al., "Induction of antigen-specific tolerance to bone marrow allografts with CD4+CD25+ T lymphocytes", Blood, vol. 103, No. 11, (2004), pp. 4216-4221.
Louis, S. et al., "Contrasting CD25hiCD4+ T cells/FOXP3 patterns in chronic rejection and operational drug-free tolerance", Transplantation, vol. 81, (2006), pp. 398-407.
Maeda, M. et al., "CD1d-independent NKT cells in beta 2-microglobulin-deficient mice have hybrid phenotype and function of NK and T cells", J. Immunol., vol. 172, (2004), pp. 6115-6122.
Maynard, C.L. et al., "Regulatory T cells expressing interleukin 10 develop from Foxp3+ and Foxp3− precursor cells in the absence of interleukin 10", Nat. Immunol., vol. 8, (2007), pp. 931-941.
Qin, W. et al., "Fusion protein of CDR mimetic peptide with Fc inhibit TNF-alpha induced cytotoxicity", Mol. Immunol., vol. 43, (2006), pp. 660-666.
Roopenian, D. et al., "The immunogenomics of minor histocompatibility antigens", Immunol. Rev., vol. 190, (2002), pp. 86-94.
Saez-Borderias, A. et al, "Expression and function of NKG2D in CD4+ T cells specific for human cytomegalovirus", Eur. J. Immunol., vol. 36, (2006), pp. 3198-3206.
Stenstrom, M. et al., "Natural killer T-cell populations in C57BL/6 and NK1.1 congenic BALB.NK mice-a novel thymic subset defined by BALB.NK mice", Immunology, vol. 114, (2005), pp. 336-345.
Sundar, S.K. et al., "Generation of Epstein-Bar virus antigen-specific suppressor T cells in vitro", Int. J. Cancer, vol. 35, (1985), pp. 351-357.
Taylor, A. et al., "T regulatory cells and allergy", Microbes and Infection, vol. 7, (2005), pp. 1049-1055.
Tsuji, N.M. et al, "Antigen-specific, CD4+CD25+ regulatory T cell clones induced in Peyer's patches", Int. Immunol., vol. 15, (2003),pp. 525-534.
Voo, K.S. et al., "Functional characterization of EBV-encoded nuclear antigen 1-specific CD4+ helper and regulatory T cells elicited by in vitro peptide stimulation", Cancer Res., vol. 65, (2005), pp. 1577-1586.
Wang, R.F., "Immune suppression by tumor-specific CD4+ regulatory T-cells in cancer", Semin. Cancer Biol., vol. 16, (2006), pp. 73-79.
Wiker, H.G. et al., "Cloning, expression and significance of MPT53 for identification of secreted proteins of *Mycobacterium tuberculosis*", Microb. Pathog., vol. 26, (1999), pp. 207-219.
Wood, K.J. et al., "Regulatory T cells in Transplantation tolerance", Nat. Rev. Immunol., vol. 3, (2003), pp. 199-210.
Haveman, L.M. et al., Induction and capture of CD4+ cytotoxic adenoviral specific T-cells in response to pan-DR binding adenoviral epitopes toward immunotherapy, Blood, vol. 106, (2005), Abstract 3238.
International Search Report for PCT/EP2009/051806, mailed Aug. 11, 2009.
Written Opinion of the International Searching Authority for PCT/EP2009/051806, mailed Aug. 11, 2009.
International Search Report for PCT/EP2009/051804, mailed Aug. 11, 2009.
Written Opinion for PCT/EP2009/051804, mailed Aug. 11, 2009.
International Search Report for PCT/EP2009/051808, mailed Feb. 18, 2010.
International Search Report for PCT/EP2009/051803, mailed Aug. 11, 2009.
Zhao et al, "Activated CD4+CD25+ T cells selectively kill B Lymphocytes", Blood, vol. 107, No. 10; pp. 3925-3932; May 15, 2006.
Canadian Office Action dated May 1, 2014, issued in connection with Canadian Patent Application No. 2,715,517.

\* cited by examiner

IMMUNOGENIC PEPTIDES AND THEIR USE IN TRANSPLANTATION

This application is the U.S. national phase of International Application No. PCT/BE2008/000010 filed 14 Feb. 2008, which designated the U.S., the entire contents of which is hereby incorporated by reference.

FIELD OF THE INVENTION

The present invention relates to immunogenic peptides and their use in suppressing and/or treating the rejection of an allograft.

BACKGROUND OF THE INVENTION

Transplantation of organs or of bone marrow is common clinical practice for the cure of organ end failure or for recovery after bone marrow failure or depletion, respectively. Organs that can be transplanted include skin, kidney, liver, heart, lung, pancreas, intestine, cornea, and even hands or parts of the face. Cellular transplantation includes bone marrow and cord blood cells, but also cells such as those of the pancreatic Langerhans beta cell islets, hepatocytes and myoblasts. New technology has recently rendered it possible to graft stem cells that have been transformed in vitro by gene reprogrammation so as to adopt the differentiation pattern of virtually any cell. This very large diversity of situations in which transplantation is mandatory is likely to increase in the coming years, both because of technology advances and because of aging populations.

A cellular and organ transplant carried out between different individuals belonging to the same species is called an allograft or allotransplant. Alloreactivity describes an immune response to allograft transplantation that is directed towards allelic differences between a host (recipient) and a donor.

The mechanism of allograft rejection is based on the recognition of alloantigens. These can be divided in 3 main categories, namely major histocompatibility complex (MHC) antigens, minor histocompatibility antigens and organ-specific alloantigens. Allograft rejection involves the recognition by allograft recipient's T lymphocytes of such alloantigens presented in the context of MHC determinants, which are presented at the surface of antigen-presenting cells (APC) together with peptides derived from the processing of alloantigens.

MHCs are divided in two categories, class I and class II, encoded by different gene loci. In man, three loci encode antigens of class I, called A, B and C, and three loci encode for class II antigens, called DP, DQ and DR. The polymorphism of MHC antigens is very high, resulting in an extremely low likelihood to find 2 unrelated individuals sharing MHC antigens.

The function of MHC antigens is to present peptides to T cells. It is classically considered that class I antigens present peptides mainly derived from cell endogenous antigens, while class II antigens present peptides generated by the processing of antigens from the outside. Distinct pathways of processing and presentation at cell surface have been described for class I as compared to class II antigen presentation. However, recent data clearly indicate that endogenously produced antigens can be efficiently presented by the MHC class II pathway, whilst exogenous antigens can be processed via the class I pathway. Hence, any protein, whether of intracellular or extracellular origin is processed into peptides that are presented to T cells by both MHC class I and class II determinants.

Peptides presented by MHC class II determinants are recognized by T cells carrying the CD4 molecule (CD4+ T cells), whilst peptides presented by MHC class I determinants are recognized by CD8+ T cells. The mechanism by which T cells recognize peptides includes 3 possibilities. T cells can recognize the peptide itself, MHC determinants, or both the peptide and MHC determinants. Crystal structures of a number of peptide-MHC-TCR complexes have shown that in allorecognition, each of these recognition modes can be observed. However, recognition of MHC determinants does not exclude the presence of a peptide, required for the stabilization of the MHC molecule at the cell surface. In such a case, however, the peptide does not necessarily differ in its amino acid sequence from corresponding peptide from the graft recipient.

APC present at their surface a large number of antigens derived from the processing of endogenous antigens, including antigens of MHCs. Thus, class II antigens present peptides from both MHC class I and MHC class II molecules, which can be recognized by allospecific T cells. Class I and class II antigens are known to be shed from the donor cells or organs, which are taken up, processed and presented by recipient's APC for T cell recognition.

In addition to major MHC antigens, minor histocompatibility antigens have been defined on their capacity to elicit cell-mediated graft rejection, but lack the structural characteristics of MHC antigens. These minor antigens are processed into peptides and presented by MHC antigens. Rejection via minor histocompatibility antigens of the donor is dependent of the polymorphism of that antigen observed between individuals belonging to the same species, as, by definition, such individuals are tolerant to their own minor histocompatibility antigens. Such antigens can be expressed ubiquitously or in a tissue- or cell-selective manner. They include surface glycoproteins, but primarily intracellular antigens such as nuclear transcription factors. One of the best examples of minor histocompatibility antigens is the one provided by antigens encoded by the Y chromosome.

In man, the importance of minor histocompatibility antigens for rejection has mostly been observed in bone marrow acceptance and in graft versus host (GVH) reactions in which immunocompetent cells from the graft are activated towards antigens of the recipient. This is because the vast majority of bone marrow transplantations are carried out with complete MHC antigens match.

The third category of antigens are tissue-specific antigens. Such antigens can present allelic variations (i.e. polymorphism) between the donor and the recipient. Allopeptides derived from tissue-specific antigens can be presented by both MHC class II and MHC class I antigens for recognition by allospecific T cells.

The mechanisms at the basis of graft rejection are usually classified in two categories, direct or indirect allorecognition. The direct pathway involves the recognition of donor antigens presented by donor APC. The indirect pathway involves the recognition of donor antigens presented by APC of the recipient. This distinction applies for the three types of alloantigens described above and is important to bear in mind for two main reasons, namely the site at which these pathways are active and the kinetics of the rejection process.

The site at which these pathways are active is different. Donor's APC contained in the graft migrate to the recipient's regional lymph nodes where they stimulate recipient T cells. By contrast, recipient APCs infiltrate the graft where they progressively replace donor APC. The type of cells presenting the antigen is not necessarily the same. For example, in the skin, the main presenting cell is the Langerhans cell, whilst in lymph nodes it is primarily conventional dendritic cells.

The distinction between the direct and indirect pathways is also important in terms of the kinetics of rejection. Thus, acute rejection is mainly the result of the direct pathway, in which recipient T cells are activated by donor APC. Recipient T cells directly recognize allelic discrepancies resulting from the polymorphism of MHC molecules. The peptide presented by the MHC molecule may present allelic variations and can thereby contribute to T cell recognition, but this is not necessarily the case. Indeed, all MHC molecules contain hundreds of peptides, only some of which present allelic variations with corresponding peptides from the recipient.

The size of the T cell repertoire is such that a highly significant proportion of all T cells (up to 1 T cell out of 10,000) is capable of reacting towards MHC allelic variations, such that this mechanism predominates the acute rejection phase. In recipients presensitized to alloantigens by previous exposure via, for instance, blood infusion or pregnancy, allo specific antibodies can also participate to the acute rejection process. In some cases, minor histocompatibility determinants can also play a role in acute rejection via the direct pathway.

Acute rejection is reduced in the clinic by matching MHC antigens between the donor and the recipient, identifying pre-sensitized recipients and, in a large majority of cases, by suppressing the capacity of the recipient of rejecting the graft with immunosuppressive drugs.

The mechanisms at the basis of chronic graft rejection are multiple, but they can also be separated into direct and indirect mechanisms. However, in many situations, the indirect pathway predominates. This is due to the progressive disappearance of donor APCs that have migrated out of the graft and the fact that cells from the graft that express MCH class I molecules induce unresponsiveness of the receiver's T cells. One exception are cells from the vascular endothelium and epithelial cells, which, under inflammatory conditions can express MHC class II molecules and thereby have the capacity to activate allospecific T cells from the recipient.

The indirect pathway is generated by alloantigens which are shed from the graft and taken up by recipient APCs for presentation to recipient cells. These antigens generate peptides that are presented into either MHC class II or class I antigens. Recent experimental evidence has shown that presentation into MHC class II antigens is most important. Mice deficient in MHC class II antigens are not able to reject a graft of a minor histocompatibility antigen-disparate donor. In man, elimination of donor APCs from the graft does not prevent chronic rejection, whilst suppression of CD4+ T cell activation with immunosuppressors such as cyclosporine significantly reduces the incidence of chronic rejection.

A likely explanation for the predominance of MHC class II presentation in the indirect pathway of chronic graft rejection is that CD8+ T cells are not easily activated by recognition of allopeptides presented by MHC class I determinants, unless help is provided by CD4+ T cells. This most likely dependent of the production of interleukin 2 (IL-2) by CD4+ T cells, required for full maturation of CD8+ T cells.

T cells of the CD4+ subtype that recognize peptides within the context of MHC class II determinants have therefore different roles: production of IL-2 for CD8+ T cell maturation into effector T cells, production of cytokines helping B cells to mature into antibody-forming cells, and infiltration of the graft in which they maintain a state of inflammation.

Graft rejection, and in particular chronic graft rejection, nowadays represents the major challenge in the clinic. It results in significant morbidity and requires maintaining graft recipients under immunosuppressive therapy with many negative side effects. There is a need to identify methods for decreasing the rate of graft rejection. This would not only be to the benefit of patients having received a graft, but also to the whole society as the cost-benefit ratio for maintaining a healthy population could be reduced.

SUMMARY OF THE INVENTION

In one aspect, the invention relates to preventing and/or treating rejection of an allograft in a recipient by administering to the recipient at least one isolated immunogenic peptide comprising (i) a T-cell epitope derived from an alloantigenic protein of an allograft and (ii) a C-(X)2-[CST] or [CST]-(X)2-C motif. Accordingly this aspect relates to the use of at least one isolated immunogenic peptide comprising (i) a T-cell epitope derived from an alloantigenic protein of an allograft and (ii) a C-(X)2-[CST] or [CST]-(X)2-C motif, for the manufacture of a medicament for preventing or treating in a recipient the rejection of said allograft.

In a further aspect, the invention relates to preventing activation of CD4+ effector T-cells of a recipient of an allograft which is caused by an alloantigenic protein derived from the allograft. Accordingly, this aspect of the invention relates to the use of at least one isolated immunogenic peptide comprising (i) a T-cell epitope derived from an alloantigenic protein of an allograft and (ii) a C-(X)2-[CST] or [CST]-(X)2-C motif, for the manufacture of a medicament for preventing activation of CD4+ effector T-cells of a recipient by an alloantigenic protein derived from said allograft.

In a further aspect, the invention relates to methods for inducing in a recipient of an allograft CD4+ regulatory T cells which are cytotoxic to cells presenting an alloantigenic protein derived from the allograft. Accordingly, the invention relates to the use of at least one isolated immunogenic peptide comprising (i) a T-cell epitope derived from an alloantigenic protein of an allograft and (ii) a C-(X)2-[CST] or [CST]-(X) 2-C motif, for the manufacture of a medicament for inducing in a recipient CD4+ regulatory T cells which are cytotoxic to cells presenting an alloantigenic protein derived from said allograft.

In a further aspect, the invention relates to methods for preventing activation of CD8+ effector T-cells of a recipient of an allograft caused by an alloantigenic protein derived from the allograft. Accordingly, the invention relates to the use of at least one isolated immunogenic peptide comprising (i) a T-cell epitope derived from an alloantigenic protein of an allograft and (ii) C-(X)2-[CST] or [CST]-(X)2-C motif, for the manufacture of a medicament for preventing activation of CD8+ effector T-cells of a recipient by an alloantigenic protein derived from said allograft.

Generally, the invention provides immunogenic peptides comprising (i) a T-cell epitope derived from an alloantigenic protein of an allograft and (ii) C-(X)2-[CST] or [CST]-(X) 2-C motif for use in preventing or treating in a recipient the rejection of the allograft, preventing activation of CD4+ and/or CD8+ effector T-cells of a recipient by an alloantigenic protein derived from the allograft and inducing in a recipient CD4+ regulatory T cells which are cytotoxic to cells presenting an alloantigenic protein derived from the allograft.

In particular embodiments of any of the herein described applications of the invention the allograft is, e.g., a bone marrow graft, a solid organ graft or a cellular graft. Solid organ grafts include kidneys, lungs, hearts, livers, pancreas, bones, skin, or soft tissues. Cellular grafts include cord blood cell graft, stem cell graft, or pancreatic islet cell graft.

In further particular embodiments to any of the herein described methods and applications the alloantigenic protein is selected from the group of minor histocompatibility antigens, major histocompatibility antigens or tissue-specific antigens. The major histocompatibility antigen is either an MHC class I-antigen or an MHC class II-antigen.

In any of the herein described uses and methods, the C-(X)2-[CST] or [CST]-(X)2-C motif present in said immunogenic peptide may be either adjacent to said T-cell epitope, or be separated from said T-cell epitope by a linker. In particular, said linker consists of at most 7 amino acids.

In further embodiments of the methods and uses described herein, the C-(X)2-[CST] or [CST]-(X)2-C motif present in the immunogenic peptide does not naturally occur within a region of 11 amino acids N- or C-terminally adjacent to the T-cell epitope in the alloantigenic protein. In particular embodiments the C-(X)2-[CST] or [CST]-(X)2-C motif is positioned N-terminally of the T-cell epitope in the immunogenic peptide.

In particular embodiments of the methods and uses described herein, at least one X in the C-(X)2-[CST] or [CST]-(X)2-C motif is Gly, Ala, Ser or Thr. Additionally or alternatively, at least one X in the motif is His or Pro. In particular embodiments of the methods and uses described herein at least one C in the C-(X)2-[CST] or [CST]-(X)2-C motif is methylated.

In particular embodiments of the immunogenic peptide used in the methods and applications described herein, the immunogenic peptide further comprises an endosomal targeting sequence. Any of the above immunogenic peptides may be produced by chemical synthesis or by recombinant expression.

A further aspect of the invention relates to methods for obtaining a population of allograft antigen-specific regulatory T cells with cytotoxic properties, the methods comprising the steps of:
providing peripheral blood cells;
contacting said cells with an immunogenic peptide comprising (i) a T-cell epitope derived from an allograft antigenic protein and (ii) a C-(X)2-[CST] or [CST]-(X)2-C motif; and
expanding said cells in the presence of IL-2.

A further method of the invention aims at obtaining a population of allograft antigen-specific regulatory T cells with cytotoxic properties, and such methods comprise the steps of:
providing an immunogenic peptide comprising (i) a T-cell epitope derived from an allograft antigenic protein and (ii) a C-(X)2-[CST] or [CST]-(X)2-C motif;
administering said immunogenic peptide to a subject; and
obtaining said population of allograft antigen-specific regulatory T cells from said subject.

Populations of allograft antigen-specific regulatory T cells with cytotoxic properties obtainable by the above methods are also part of the invention, as well as their use for the manufacture of a medicament for preventing or treating in a recipient the rejection of an allograft.

A further aspect of the invention relates to any of the above uses or methods wherein said alloantigenic protein or allograft antigen is the Dby antigen encoded by the H—Y chromosome.

The invention also relates to isolated immunogenic peptides comprising a T-cell epitope from the Dby antigen and, adjacent to said T-cell epitope or separated from said T-cell epitope by a linker, a C-(X)2-[CST] or [CST]-(X)2-C motif.

DETAILED DESCRIPTION OF THE INVENTION

Definitions

The term "peptide" when used herein refers to a molecule comprising an amino acid sequence of between 2 and 200 amino acids, connected by peptide bonds, but which can, in particular embodiments, comprise non-amino acid structures (like for example a linking organic compound). Peptides according to the invention can contain any of the conventional 20 amino acids or modified versions thereof, or can contain non-naturally occurring amino acids incorporated by chemical peptide synthesis or by chemical or enzymatic modification.

The term "epitope" when used herein refers to one or several portions (which may define a conformational epitope) of a protein which is/are specifically recognized and bound by an antibody or a portion thereof (Fab', Fab2', etc.) or a receptor presented at the cell surface of a B or T cell lymphocyte, and which is able, by said binding, to induce an immune response.

The term "antigen" when used herein refers to a structure of a macromolecule comprising one or more hapten(s) (eliciting an immune response only when attached to a carrier) and/or comprising one or more T cell epitopes.
Typically, the macromolecule is a protein or peptide (with or without polysaccharides) or a molecule of proteic composition and comprises one or more epitopes; the macromolecule can herein alternatively be referred to as "antigenic protein" or "antigenic peptide".

The terms "alloantigen" or "allograft antigen" when used herein refer to an antigen derived from (shed from and/or present in) a cell or tissue which, when transferred from a donor to a recipient, can be recognized and bound by an antibody or B or T-cell receptor of the recipient. Allogens are typically products of polymorphic genes. An alloantigen is a protein or peptide which, when compared between donor and recipient (belonging to the same species), displays slight structural differences. The presence of such donor antigen in the body of a recipient can elicit an immune response in the recipient. Such alloreactive immune response is specific for the alloantigen.

The term alloantigen further encompasses antigens derived from (shed from and/or present in) a graft transferred from a donor to a recipient, which antigens are absent in the recipient.

The term "alloreactivity" when used herein refers to an immune response that is directed towards allelic differences between the graft recipient and the donor. Alloreactivity applies to antibodies and to T cells.

The present invention relies on T cell alloreactivity, which is based on T cell recognition of alloantigens presented in the context of MHC determinants as peptide-MHC complexes.

The term "allograft" when used herein refers to any cell or group of cells, whether or not organized in an organ of part of an organ, that is removed from a donor and is transferred, grafted or transplanted to/in a recipient belonging to the same species as the donor.

The terms "donor" and "recipient" refer respectively to the individual providing a graft and the individual receiving this same graft. These individuals are mammals, in particular primates or humans. Typically donor and recipient are different individuals belonging to the same species.

The term "allograft rejection" when used herein refers to any mechanism whereby the immune system of the recipient reacts to the allograft (i.e., is alloreactive) and thereby gradually destroys the integrity and/or functionality of the allograft.

The term "T cell epitope" or "T-cell epitope" in the context of the present invention refers to a dominant, sub-dominant or minor T cell epitope, i.e., a part of an antigenic protein that is specifically recognized and bound by a receptor at the cell surface of a T lymphocyte.

Whether an epitope is dominant, sub-dominant or minor depends on the immune reaction elicited against the epitope. Dominance depends on the frequency at which such epitopes are recognized by T cells and able to activate them, among all the possible T cell epitopes of a protein. In particular, a T cell epitope is an epitope bound by MHC class I or MHC class II molecules.

The term "MHC" refers to "major histocompatibility antigen". In humans, the MHC genes are known as HLA ("human leukocyte antigen") genes.

Although there is no consistently followed convention, some literature uses "HLA" to refer to HLA protein molecules, and "MHC" to refer to the genes encoding the HLA proteins. As such the terms "MHC" and "HLA" are equivalents when used herein. The HLA system in man has its equivalent in the mouse, i.e., the H2 system. The most intensely-studied HLA genes are the nine so-called classical MHC genes: HLA-A, HLA-B, HLA-C, HLA-DPA1, HLA-DPB1, HLA-DQA1, HLA-DQB1, HLA-DRA, HLA-DRB1. In humans, the MHC is divided into three regions: Class I, II, and III. The A, B, and C genes belong to MHC class I, whereas the six D genes belong to class II. MHC class I molecules are made of a single polymorphic chain containing 3 domains (alpha 1, 2 and 3), which associates with beta 2 microglobulin at cell surface. Class II molecules are made of 2 polymorphic chains, each containing 2 chains (alpha 1 and 2, and beta 1 and 2).

Class I MHC molecules are expressed on virtually all nucleated cells. Peptide fragments presented in the context of class I MHC molecules are recognized by CD8+ T lymphocytes (cytotoxic T lymphocytes or CTLs). CD8+ T lymphocytes frequently mature into cytotoxic effectors which can lyse cells bearing the stimulating antigen. Class II MHC molecules are expressed primarily on activated lymphocytes and antigen-presenting cells. CD4+ T lymphocytes (helper T lymphocytes or HTLs) are activated with recognition of a unique peptide fragment presented by a class II MHC molecule, usually found on an antigen presenting cell like a macrophage or dendritic cell. CD4+ T lymphocytes proliferate and secrete cytokines that either support an antibody-mediated response through the production of IL-4 and IL-10 or support a cell-mediated response through the production of IL-2 and IFN-gamma.

Functional HLAs are characterized by a deep binding groove to which endogenous as well as foreign, potentially antigenic peptides bind. The groove is further characterized by a well-defined shape and physico-chemical properties. HLA class I binding sites are closed, in that the peptide termini are pinned down into the ends of the groove. They are also involved in a network of hydrogen bonds with conserved HLA residues. In view of these restraints, the length of bound peptides is limited to 8-10 residues. However, it has been demonstrated that peptides of up to 12 amino acid residues are also capable of binding HLA class I. Superposition of the structures of different HLA complexes confirmed a general mode of binding wherein peptides adopt a relatively linear, extended conformation.

In contrast to HLA class I binding sites, class II sites are open at both ends. This allows peptides to extend from the actual region of binding, thereby "hanging out" at both ends. Class II HLAs can therefore bind peptide ligands of variable length, ranging from 9 to more than 25 amino acid residues.

Similar to HLA class I, the affinity of a class II ligand is determined by a "constant" and a "variable" component. The constant part again results from a network of hydrogen bonds formed between conserved residues in the HLA class II groove and the main-chain of a bound peptide. However, this hydrogen bond pattern is not confined to the N- and C-terminal residues of the peptide but distributed over the whole chain. The latter is important because it restricts the conformation of complexed peptides to a strictly linear mode of binding. This is common for all class II allotypes. The second component determining the binding affinity of a peptide is variable due to certain positions of polymorphism within class II binding sites. Different allotypes form different complementary pockets within the groove, thereby accounting for subtype-dependent selection of peptides, or specificity. Importantly, the constraints on the amino acid residues held within class II pockets are in general "softer" than for class I. There is much more cross reactivity of peptides among different HLA class II allotypes. The sequence of the +/−9 amino acids of an MHC class II T cell epitope that fit in the groove of the MHC II molecule are usually numbered P1 to P9. Additional amino acids N-terminal of the epitope are numbered P-1, P-2 and so on, amino acids C-terminal of the epitope are numbered P+1, P+2 and so on.

The term "minor histocompatibility antigen" refers to peptides that are derived from normal cellular proteins and are presented by MHC belonging to the class I and/or the class II complexes. Any genetic polymorphism that qualitatively or quantitatively affects the display of such peptides at the cell surface can give rise to a minor histocompatibility antigen.

The term "organic compound having a reducing activity" when used herein refers to compounds, more in particular amino acid sequences, capable of reducing disulfide bonds in proteins. An alternatively used term for these amino acid sequences is "redox motif".

The term "therapeutically effective amount" refers to an amount of the peptide of the invention or derivative thereof, which produces the desired therapeutic or preventive effect in a patient.

For example, in reference to a disease or disorder, it is the amount which reduces to some extent one or more symptoms of the disease or disorder, and more particularly returns to normal, either partially or completely, the physiological or biochemical parameters associated with or causative of the disease or disorder. According to one particular embodiment of the present invention, the therapeutically effective amount is the amount of the peptide of the invention or derivative thereof, which will lead to an improvement or restoration of the normal physiological situation. For instance, when used to therapeutically treat a mammal affected by an immune disorder, it is a daily amount peptide/kg body weight of the said mammal. Alternatively, where the administration is through gene-therapy, the amount of naked DNA or viral vectors is adjusted to ensure the local production of the relevant dosage of the peptide of the invention, derivative or homologue thereof.

The term "natural" when used herein referring to a sequence relates to the fact that the sequence is identical to a naturally occurring sequence.

In contrast therewith the term "artificial" refers to a sequence which as such does not occur in nature. Unless otherwise specified, the terms natural and artificial thus exclusively relate to a particular amino acid (or nucleotide) sequence (e.g. the sequence of the immunogenic peptide, a sequence comprised within the immunogenic peptide, an epitope sequence) and do not refer to the nature of the immunogenic peptide as such.

Optionally, an artificial sequence is obtained from a natural sequence by limited modifications such as changing one or more amino acids within the naturally occurring sequence or by adding amino acids N- or C-terminally of a naturally occurring sequence. Amino acids are referred to herein with their full name, their three-letter abbreviation or their one letter abbreviation.

Motifs of amino acid sequences are written herein according to the format of Prosite. The symbol X is used for a position where any amino acid is accepted. Alternatives are indicated by listing the acceptable amino acids for a given position, between square brackets ('[ ]'). For example: [CST] stands for an amino acid selected from Cys, Ser or Thr. Amino acids which are excluded as alternatives are indicated by listing them between curly brackets ('{ }'). For example: {AM} stands for any amino acid except Ala and Met. The different elements in a motif are separated from each other by a hyphen-. Repetition of an identical element within a motif can be indicated by placing behind that element a numerical value or a numerical range between parentheses. For example: X(2) corresponds to X-X, X(2, 4) corresponds to X-X or X-X-X or X-X-X-X, A(3) corresponds to A-A-A.

The term "homologue" when used herein with reference to the epitopes used in the context of the invention, refer to molecules having at least 50%, at least 70%, at least 80%, at least 90%, at least 95% or at least 98% amino acid sequence identity with the naturally occurring epitope, thereby maintaining the ability of the epitope to bind an antibody or cell surface receptor of a B and/or T cell. Particular embodiments of homologues of an epitope correspond to the natural epitope modified in at most three, more particularly in at most two, most particularly in one amino acid.

The term "derivative" when used herein with reference to the peptides of the invention refers to molecules which contain at least the peptide active portion (i.e. capable of eliciting cytolytic CD4+ T cell activity) and, in addition thereto comprises a complementary portion which can have different purposes such as stabilizing the peptides or altering the pharmacokinetic or pharmacodynamic properties of the peptide.

The term "sequence identity" of two sequences when used herein relates to the number of positions with identical nucleotides or amino acids divided by the number of nucleotides or amino acids in the shorter of the sequences, when the two sequences are aligned. In particular embodiments, said sequence identity is from 70% to 80%, from 81% to 85%, from 86% to 90%, from 91% to 95%, from 96% to 100%, or 100%.

The terms "peptide-encoding polynucleotide (or nucleic acid)" and "polynucleotide (or nucleic acid) encoding peptide" when used herein refer to a nucleotide sequence, which, when expressed in an appropriate environment, results in the generation of the relevant peptide sequence or a derivative or homologue thereof. Such polynucleotides or nucleic acids include the normal sequences encoding the peptide, as well as derivatives and fragments of these nucleic acids capable of expressing a peptide with the required activity. According to one embodiment, the nucleic acid encoding the peptides according to the invention or fragment thereof is a sequence encoding the peptide or fragment thereof originating from a mammal or corresponding to a mammalian, most particularly a human peptide fragment.

DETAILED DESCRIPTION

In work leading to the present invention it was initially observed that, in one of the most studied models of graft rejection, the graft rejection could be prevented by pre-immunization of the recipient individual (syngeneic with the donor individual) with an immunogenic peptide, without requiring immunosuppression. The immunogenic peptide capable of ensuring this effect is a peptide comprising a single T cell epitope derived from an allograft antigenic protein, linked to a redox motif such as C-(X)2-C. Clearly this observation opens a whole new avenue of possibilities to prevent and/or treat allograft rejection in a recipient and/or to condition the recipient's immune system such that the risk or likelihood of allograft rejection is significantly reduced or lowered, or is even completely eliminated.

A first aspect of the invention relates to the use of at least one isolated immunogenic peptide according to the invention for preventing or treating in a mammalian recipient, the rejection of an allograft. More particularly the invention relates to the use of an immunogenic peptide comprising (i) a T-cell epitope derived from an alloantigenic protein of an allograft of a mammal and (ii) a C-(X)2-[CST] or [CST]-(X)2-C motif, for the manufacture of a medicament for preventing or treating in a mammalian recipient, the rejection of the allograft. Hence, the immunogenic peptide or the medicament comprising it can be used for prior or prophylactic treatment or immunization of a recipient of an allograft in order to suppress, avoid, reduce partially or totally, or eliminate (partially or totally) rejection (acute or chronic) of the subsequently transferred allograft. Likewise, the immunogenic peptide or the medicament comprising it can be used for therapeutic treatment or immunization of a recipient of an allograft in order to suppress, reduce partially or totally, or eliminate (partially or totally) ongoing rejection, such as chronic rejection, of said allograft.

It was further observed that CD4+ T-cells, in particular CD4+ effector T-cells, and CD8+ T-cells of the individual pre-treated or pre-immunized with the immunogenic peptide comprising the allograft T cell epitope modified as described above were not activated upon actual receipt of the allograft. In contrast therewith, a population of CD4+ regulatory T-cells (Tregs) was induced that displays cytotoxicity toward antigen-presenting cells (APCs) presenting an alloantigen derived from the allograft.

Hence, a further aspect of the invention relates to the use of at least one isolated immunogenic peptide according to the invention for preventing activation of CD4+ effector T-cells of a recipient of an allograft caused by an alloantigenic protein derived from the allograft. Accordingly, the invention relates to the use of immunogenic peptides comprising (i) a T-cell epitope derived from an alloantigenic protein of an allograft and (ii) a C-(X)2-[CST] or [CST]-(X)2-C motif, for the manufacture of a medicament for preventing activation of CD4+ effector T-cells of a recipient by an alloantigenic protein derived from said allograft.

In a further aspect, the current invention envisages the use of at least one isolated immunogenic peptide for inducing in a recipient of an allograft CD4+ regulatory T cells which are cytotoxic to cells presenting an alloantigenic protein derived from the allograft. More particularly, the invention envisages the use of an immunogenic peptide according to the invention comprising (i) a T-cell epitope derived from an alloantigenic protein of an allograft and (ii) a C-(X)2-[CST] or [CST]-(X)2-C motif, for the manufacture of a medicament for inducing in a recipient CD4+ regulatory T cells which are cytotoxic to cells presenting an alloantigenic protein derived from the allograft.

A further aspect of the invention covers the use of at least one isolated immunogenic peptide according to the invention comprising (i) a T-cell epitope derived from an alloantigenic protein of an allograft and (ii) C-(X)2-[CST] or [CST]-(X)

2-C motif, for the manufacture of a medicament for preventing activation of CD8+ effector T-cells of a recipient by an alloantigenic protein derived from said allograft.

In the above aspects of the invention, the immunogenic peptide or the medicament comprising it can be used for prior or prophylactic treatment or immunization of a recipient of an allograft in order to suppress, avoid, reduce partially or totally, or eliminate (partially or totally) a normally expected activation in the recipient of CD4+ effector T-cells and/or CD8+ T-cells following or subsequent to the actual allograft transfer. Likewise, said immunogenic peptide or the medicament comprising it can be used for therapeutic treatment or immunization of a recipient of an allograft in order to suppress, reduce partially or totally, or eliminate (partially or totally) activation in the recipient of CD4+ effector T-cells and/or CD8+ T-cells concurrent with or after the actual allograft transfer. Alternatively, or concurrently with any of the above, said immunogenic peptide or the medicament comprising it can be used for prior or prophylactic treatment or immunization of a recipient of an allograft in order to induce a normally unexpected activation in the recipient of allograft-specific CD4+ regulatory T-cells capable of killing cells presenting alloantigen(s) following or subsequent to the actual allograft transfer. Likewise, said immunogenic peptide or the medicament comprising it can be used for therapeutic treatment or immunization of a recipient of an allograft in order to induce activation in the recipient of allo graft-specific CD4+ regulatory T-cells capable of killing cells presenting alloantigen(s). Said induction may happen concurrent with or after the actual allograft transfer.

In any of the uses described hereinabove, the recipient is a mammal, in particular a (non-human) primate or a human.

In particular embodiments to the above the allograft is a solid organ graft or a cellular graft. Solid organ grafts include kidneys, lungs, hearts, livers, pancreas, bones, skin, or soft tissues. Cellular grafts include e.g., a bone marrow graft, cord blood cell graft, stem cell graft, pancreatic islet cell graft, or blood cell transfusion (in particular in view of possible immune reactions towards granulocytes).

In further particular embodiments of any of the methods described herein, said alloantigenic protein is selected from the group of minor histocompatibility antigens, major histocompatibility antigens or tissue-specific antigens. Where the alloantigenic protein is a major histocompatibility antigen, this is either an MHC class I-antigen or an MHC class II-antigen. An important point to keep in mind is the variability of the mechanisms by which alloantigen-specific T cells recognize cognate peptides at the surface of APC. As stated above (see background of the invention), alloreactive T cells can recognize either alloantigen-determinants of the MHC molecule itself, an alloantigen peptide bound to a MHC molecule of either autogenic or allogeneic source, or a combination of residues located within the alloantigen-derived peptide and the MHC molecule, the latter being of autogenic or allogeneic origin. This contrasts with the situation encountered with immune responses towards nominal antigens, in which T cells are activated by binding to determinants located within both the peptide of allogeneic source and self MHC molecule (conventional responses) or binding to determinants that are located in both a self-derived peptide and a self MHC molecule (as seen in autoimmune responses).

According to the present invention, alloantigen peptides coupled to a redox motif are used to reduce allograft rejection. These peptides are peptides which can be presented by either allogeneic MHC determinants (referred to as the direct pathway of allo-recognition) or by self-MHC molecules (referred to as the indirect pathway of allo-recognition). The mechanisms underlying the present invention involve alloantigen peptides (including alloantigen peptides derived from MHC class I and class II molecules) which are presented by MHC class II determinants of allogeneic or autogenic source. Accordingly, as this does not necessarily require that alloreactive T cells recognize determinants located in both the alloantigen peptide and MHC molecule, the alloantigen peptides can be selected independently.

According to particular embodiments, allogenic peptides are peptides obtained from minor histocompatibility antigens.

Methods for identifying suitable allogenic peptides from minor histocompatibility antigens are known in the art. For instance these can be obtained directly by elution from APC and testing for their capacity to activate CD4+ T cells. The source of such T cells is from donors who have been sensitized to the minor histocompatibility antigens either by transfusion of blood or cells, pregnancy, or by exposure to tissue grafts expressing the minor histocompatibility antigens. The specific T cells can be polyclonal, oligoclonal or monoclonal and used in a suitable T cell proliferation assay described below.

Examples of minor histocompatibility antigens are those derived from proteins encoded by the HY chromosome (H—Y antigens). Other examples can be found in, for instance, Goulmy E, Current Opinion in Immunology, vol 8, 75-81, 1996 (see Table 3 therein in particular); It has to be noted that many minor histocompatibility antigens in man have been detected via their presentation into MHC class I determinants by use of cytolytic CD8+ T cells. However, such peptides are derived by the processing of proteins that also contain MHC class II restricted T cell epitopes, thereby providing the possibility of designing peptides of the present invention.

In further particular embodiments, the allogenic peptide is a tissue specific alloantigen. Tissue-specific alloantigens can be identified using the same procedure. One example of this is the MHC class I restricted epitope derived from a protein expressed in kidneys but not in spleen and capable of eliciting CD8+ T cells with cytotoxic activity on kidney cells (Poindexter et al, Journal of Immunology, 154: 3880-3887, 1995).

In further particular embodiments, the allogenic peptide is an MHC alloantigen. Examples of peptides encompassing MHC class II T cell epitopes derived from MHC class II antigens are found in Benichou et al, Journal of Experimental Medicine, 175: 305-308, 1192, and in Liu et al, Journal of Immunology, 150: 3180-3186, 1993. Peptides derived from MHC class I antigens and presented by MHC class II antigens are described in Tam et al, Journal of Immunology, 156: 3765-3771, 1996.

Cytotoxic regulatory T cells elicited by the immunogenic peptides of the present invention can suppress immune responses to even complex alloantigens. A minimum requirement for such cells to be activated is to recognize a cognate peptide presented by MHC class II determinants, leading to apoptosis of the APC, thereby suppressing the responses of T cells (both CD4+ and CD8+ T cells) to all T cell epitopes presented by the APC. An additional mechanism by which cytotoxic regulator T cells can suppress the overall immune response towards complex antigens is by suppressing the activation of bystander T cells.

In some situations, more than one alloantigen participates in the rejection process. Under such circumstances, the same APC may not present all relevant alloantigens, as some of such alloantigens are shed from the graft and taken up by potentially different APCs. It is therefore anticipated that combination of two or more immunogenic peptides derived from the same or different alloantigens may be used for the prevention and treatment of graft rejection.

A further aspect of the invention relates to uses and methods as described hereinabove, wherein the immunogenic peptide is replaced by CD4+ regulatory T-cells primed with the immunogenic peptide, or by a nucleotide sequence encoding the immunogenic peptide (e.g. in the form of naked DNA or a viral vector to be administered to an individual instead of the immunogenic peptide). In addition, a combination of multiple immunogenic peptides, i.e. more than 1 (e.g., 2, 3, 4, 5, 6, 7, 8, 9, 10 or more), can be used in any of the above. These aspects of the invention, as well as the further modification of the immunogenic peptide are described in detail hereafter.

The present invention is based upon the finding that an immunogenic peptide, comprising a T cell epitope derived from an alloantigen and a peptide sequence having reducing activity is capable of generating a population of CD4+ regulatory T cells, which have a cytotoxic effect on antigen presenting cells. It is additionally based upon the finding that such immunogenic peptide is capable of preventing activation of alloantigen-specific CD8+ T cells and/or CD4+ effector T cells.

Accordingly, the invention relates to immunogenic peptides, which comprise at least one T-cell epitope of an alloantigen with a potential to trigger an immune reaction, coupled to an organic compound having a reducing activity, such as a peptide with a thioreductase sequence motif. The T cell epitope and the organic compound are optionally separated by a linker (eg an organic spacer molecule or a peptide sequence). In further optional embodiments the immunogenic peptide additionally comprises an endosome targeting sequence (e.g. late endosomal targeting sequence) and/or additional "flanking" sequences.

The immunogenic peptides of the invention can be schematically represented as A-L-B or B-L-A, wherein A represents a T-cell epitope of an antigen (self or non-self) with a potential to trigger an immune reaction, L represents a linker and B represents an organic compound having a reducing activity.

The reducing activity of an organic compound can be assayed for its ability to reduce a sulfhydryl group such as in the insulin solubility assay known in the art, wherein the solubility of insulin is altered upon reduction, or with a fluorescence-labelled insulin. The reducing organic compound may be coupled at the amino-terminus side of the T-cell epitope or at the carboxy-terminus of the T-cell epitope.

Generally the organic compound with reducing activity is a peptide. Peptide fragments with reducing activity are encountered in thioreductases which are small disulfide reducing enzymes including glutaredoxins, nucleoredoxins, thioredoxins and other thiol/disulfide oxydoreductases They exert reducing activity for disulfide bonds on proteins (such as enzymes) through redox active cysteines within conserved active domain consensus sequences: C-X(2)-C, C-X(2)-S, C-X(2)-T, S—X(2)-C, T-X(2)-C (Fomenko et al. (2003) *Biochemistry* 42, 11214-11225), in which X stands for any amino acid. Such domains are also found in larger proteins such as protein disulfide isomerase (PDI) and phosphoinositide-specific phospholipase C.

Accordingly, in particular embodiments, immunogenic peptides for use in accordance with the present invention comprise as redox motif the thioreductase sequence motif C-(X)2-[CST] or [CST]-(X)2-C. In a further embodiment the C-(X)2-[CST] or [CST]-(X)2-C motif is positioned N-terminally of the T-cell epitope. In the present application such a tetrapeptide will be referred to as “the motif”. In particular embodiments peptides of the invention contain the sequence motif C-X(2)-[CS] or [CS]—X(2)-C. In more particular embodiments peptides contain the sequence motif C—X(2)-S, S—X(2)-C or C-X(2)-C.

As explained in detail further on, the immunogenic peptides of the present invention can be made by chemical synthesis, which allows the incorporation of non-natural amino acids. Accordingly, in the motif of reducing compounds according to particular embodiments of the present invention, C represents either cysteine or another amino acids with a thiol group such as mercaptovaline, homocysteine or other natural or non-natural amino acids with a thiol function. In order to have reducing activity, the cysteines present in the motif should not occur as part of a cystine disulfide bridge. Nevertheless, the motif may comprise modified cysteines such as methylated cysteine, which is converted into cysteine with free thiol groups in vivo.

Each of the amino acids X in the C-(X)2-[CST] or [CST]-(X)2-C motif of particular embodiments of the reducing compounds of the invention can be any natural amino acid, including S, C, or T or can be a non-natural amino acid, whereby the two amino acids X are either the same or different. In particular embodiments X is an amino acid with a small side chain such as Gly, Ala, Ser or Thr. In further particular embodiments, X is not an amino acid with a bulky side chain such as Tyr. In further particular embodiments at least one X in the [CST]-X(2)-[CST] motif is His or Pro.

In the immunogenic peptides of the present invention comprising the (redox) motif described above, the motif is located such that, when the epitope fits into the MHC groove, the motif remains outside of the MHC binding groove. The motif is placed either immediately adjacent to the epitope sequence within the peptide, or is separated from the T cell epitope by a linker. More particularly, the linker comprises an amino acid sequence of 7 amino acids or less. Most particularly, the linker comprises 1, 2, 3, or 4 amino acids. Alternatively, a linker may comprise 6, 8 or 10 amino acids. Typical amino acids used in linkers are serine and threonine. Example of peptides with linkers in accordance with the present invention are CXXC-G-epitope (SEQ ID NO:14), CXXC-GG-epitope (SEQ ID NO:15), CXXC-SSS-epitope (SEQ ID NO:16), CXXC-SGSG-epitope (SEQ ID NO:17) and the like.

In those particular embodiments of the peptides of the invention where the motif sequence is adjacent to the epitope sequence, this is indicated as position P-4 to P-1 or P+1 to P+4 compared to the epitope sequence. Apart from a peptide linker other organic compounds can be used as linker to link the parts of the immunogenic peptide to each other.

The immunogenic peptides of the present invention can further comprise additional short amino acid sequences N or C-terminally of the (artificial) sequence comprising the T cell epitope and the reducing compound (motif). Such an amino acid sequence is generally referred to herein as a ‘flanking sequence’. A flanking sequence can be positioned N- and/or C-terminally of the redox motif and/or of the T-cell epitope in the immunogenic peptide. When the immunogenic peptide comprises an endosomal targeting sequence, a flanking sequence can be present between the epitope and an endosomal targeting sequence and/or between the reducing compound (e.g. motif) and an endosomal targeting sequence. More particularly a flanking sequence is a sequence of up to 10 amino acids, or of in between 1 and 7 amino acids, such as a sequence of 2 amino acids.

In particular embodiments of the invention, the redox motif in the immunogenic peptide is located N-terminally from the epitope.

In further particular embodiments, where the redox motif present in the immunogenic peptide contains one cysteine, this cysteine is present in the motif in the position most remote from the epitope, thus the motif occurs as C-X(2)-[ST] or C-X(2)-S N-terminally of the epitope or occurs as [ST]-X(2)-C or S—X(2)-C carboxy-terminally of the epitope.

In certain embodiments of the present invention, immunogenic peptides are provided comprising one epitope sequence and a motif sequence. In further particular embodiments, the motif occurs several times (1, 2, 3, 4 or even more times) in the peptide, for example as repeats of the motif which can be spaced from each other by one or more amino acids (e.g. CXXC X CXXC X CXXC [SEQ ID. NO:1]), as repeats which are adjacent to each other (CXXC CXXC CXXC [SEQ ID. NO:2]) or as repeats which overlap with each other CXX-CXXCXXC [SEQ ID. NO:3] or CXCCXCCXCC [SEQ ID. NO:4]). Alternatively, one or more motifs are provided at both the N and the C terminus of the T cell epitope sequence. Other variations envisaged for the immunogenic peptides of the present invention include peptides containing repeats of a T cell epitope sequence or multiple different T-cell epitopes wherein each epitope is preceded and/or followed by the motif (e.g. repeats of "motif-epitope" or repeats of "motif-epitope-motif"). Herein the motifs can all have the same sequence but this is not obligatory. It is noted that repetitive sequences of peptides which comprise an epitope which in itself comprises the motif will also result in a sequence comprising both the 'epitope' and a 'motif'. In such peptides, the motif within one epitope sequence functions as a motif outside a second epitope sequence. In particular embodiments however, the immunogenic peptides of the present invention comprise only one T cell epitope.

As describe above the immunogenic peptides according to the invention comprise, in addition to a reducing compound/motif, a T cell epitope derived from an alloantigen. A T cell epitope in a protein sequence can be identified by functional assays and/or one or more in silico prediction assays. The amino acids in a T cell epitope sequence are numbered according to their position in the binding groove of the MHC proteins. In particular embodiments, the T-cell epitope present within the peptides of the invention consists of between 8 and 25 amino acids, yet more particularly of between 8 and 16 amino acids, yet most particularly consists of 8, 9, 10, 11, 12, 13, 14, 15 or 16 amino acids. In a more particular embodiment, the T cell epitope consists of a sequence of 9 amino acids. In a further particular embodiment, the T-cell epitope is an epitope, which is presented to T cells by MHC-class II molecules. In particular embodiments of the present invention, the T cell epitope sequence is an epitope sequence which fits into the cleft of an MHC II protein, more particularly a nonapeptide fitting into the MHC II cleft. The T cell epitope of the immunogenic peptides of the invention can correspond either to a natural epitope sequence of a protein or can be a modified version thereof, provided the modified T cell epitope retains its ability to bind within the MHC cleft, similar to the natural T cell epitope sequence. The modified T cell epitope can have the same binding affinity for the MHC protein as the natural epitope, but can also have a lowered affinity. In particular embodiments the binding affinity of the modified peptide is no less than 10-fold less than the original peptide, more particularly no less than 5 times less. It is a finding of the present invention that the peptides of the present invention have a stabilizing effect on protein complexes. Accordingly, the stabilizing effect of the peptide-MHC complex compensates for the lowered affinity of the modified epitope for the MHC molecule.

In particular embodiments, the immunogenic peptides of the invention further comprise an amino acid sequence (or another organic compound) facilitating uptake of the peptide into (late) endosomes for processing and presentation within MHC class II determinants. The late endosome targeting is mediated by signals present in the cytoplasmic tail of proteins and correspond to well-identified peptide motifs such as the dileucine-based [DE]XXXL[LI] or DXXLL motif (e.g. DXXXLL), the tyrosine-based YXXØ motif or the so-called acidic cluster motif. The symbol Ø represents amino acid residues with a bulky hydrophobic side chains such as Phe, Tyr and Trp. The late endosome targeting sequences allow for processing and efficient presentation of the antigen-derived T cell epitope by MHC-class II molecules. Such endosomal targeting sequences are contained, for example, within the gp75 protein (Vijayasaradhi et al. (1995) *J Cell Biol* 130, 807-820), the human CD3 gamma protein, the HLA-BM β (Copier et al. (1996) *J. Immunol.* 157, 1017-1027), the cytoplasmic tail of the DEC205 receptor (Mahnke et al. (2000) *J Cell Biol* 151, 673-683). Other examples of peptides which function as sorting signals to the endosome are disclosed in the review of Bonifacio and Traub (2003) *Annu. Rev. Biochem.* 72, 395-447. Alternatively, the sequence can be that of a subdominant or minor T cell epitope from a protein, which facilitates uptake in late endosome without overcoming the T cell response towards the alloantigen-derived T cell epitope.

The immunogenic peptides of the invention can be generated by coupling a reducing compound, more particularly a reducing motif as described herein, N-terminally or C-terminally to a T-cell epitope of an alloantigenic protein (either directly adjacent thereto or separated by a linker). Moreover the T cell epitope sequence of the immunogenic peptide and/or the redox motif can be modified and/or one or more flanking sequences and/or a targeting sequence can be introduced (or modified), compared to the naturally occurring T-cell epitope sequence. Accordingly, the resulting sequence of the immunogenic peptide will in most cases differ from the sequence of the alloantigenic protein of interest. In this case the immunogenic peptides of the invention are peptides with an 'artificial', non-naturally occurring sequence.

The immunogenic peptides of the invention can vary substantially in length, e.g. from about 12-13 amino acids (a T-cell epitope of 8-9 amino acids and the 4-amino acid redox motif) to up to 50 or more amino acids. For example, an immunogenic peptide according to the invention may comprise an endosomal targeting sequence of 40 amino acids, a flanking sequence of about 2 amino acids, a motif as described herein of 4 amino acids, a linker of 4 amino acids and a T cell epitope peptide of 9 amino acids. In particular embodiments, the immunogenic peptides of the invention consist of between 12 amino acids and 20 up to 25, 30, 50, 75, 100 or 200 amino acids. In a more particular embodiment, the peptides consist of between 10 and 20 amino acids. More particularly, where the reducing compound is a redox motif as described herein, the length of the immunogenic peptide comprising the epitope and motif optionally connected by a linker is 19 amino acids or less, e.g., 12, 13, 14, 15, 16, 17 or 18 amino acids.

As detailed above, the immunogenic peptides for use in the reduction or prevention of allograft rejection according to the invention comprise a reducing motif as described herein linked to a T cell epitope sequence. According to particular embodiments, the T-cell epitopes are derived from alloantigens which do not naturally comprise an amino acid sequence with redox properties within a sequence of 11 amino acids N- or C-terminally adjacent to the T-cell epitope of interest. Most particularly, the invention encompasses generating immunogenic peptides from alloantigenic proteins which do not comprise a sequence selected from C-X(2)-S, S—X(2)-C, C-X (2)-C, S—X(2)-S, C-X(2)-T, T-X(2)-C within a sequence of 11 amino acids N- or C-terminally of the epitope sequence. In further particular embodiments, the present invention provides immunogenic peptides of alloantigenic proteins for use in the treatment of allograft rejection and the generation of allograft antigen specific regulatory T cells, whereby the alloantigenic proteins do not comprise the above-described amino acid sequences with redox properties within their sequence.

In further particular embodiments, the immunogenic peptides of the invention are peptides comprising T cell epitopes which do not comprise an amino acid sequence with redox properties within their natural sequence. However, in alternative embodiments, a T cell epitope binding to the MHC cleft may comprise a redox motif such as described herein within its epitope sequence; the immunogenic peptides for use according to the invention comprising such T-cell epitope must further comprise another redox motif coupled (adjacent of separated by a linker) N- or C-terminally to the epitope such that the attached motif can ensure the reducing activity (contrary to the motif present in the epitope, which is buried within the cleft).

Another aspect of the present invention relates to methods for generating immunogenic peptides of the present invention described herein. Such methods include the identification of T-cell epitopes in an alloantigenic protein of interest. Ways for in vitro and in silky identification T-cell epitopes are amply known in the art and some aspects are elaborated upon hereafter. The generated immunogenic peptides are optionally assessed for the capability to induce alloantigen-specific CD4+ regulatory T cells which are cytotoxic for cells presenting (parts of) the alloantigenic protein of interest.

Immunogenic peptides according to the invention are generated using T-cell epitopes of the allogeneic proteins of interest. The alloantigens that can be used for selection of T-cell epitopes are typically alloantigens, which are selected from the group consisting of MHC class I antigens, MHC class II antigens, minor histocompatibility antigens or tissue-specific alloantigens. In particular embodiments, the T-cell epitope used is a dominant T-cell epitope.

The identification and selection of a T-cell epitope from alloantigens, for use in the context of the present invention optionally involve one or more of the following methods. For instance, peptide sequences isolated from an alloantigenic protein are tested by, for example, T cell biology techniques, to determine whether the peptide sequences elicit a T cell response. Those peptide sequences found to elicit a T cell response are defined as having T cell stimulating activity. Human T cell stimulating activity can further be tested by culturing T cells obtained from an individual sensitized to an alloantigen with a peptide/epitope derived from the allo-antigen and determining whether proliferation of T cells occurs in response to the peptide/epitope. This can be measured, e.g., by cellular uptake of tritiated thymidine. Stimulation indices for responses by T cells to peptides/epitopes can be calculated as the maximum CPM in response to a peptide/epitope divided by the control CPM. A T cell stimulation index (S.I.) equal to or greater than two times the background level is considered "positive." Positive results are used to calculate the mean stimulation index for each peptide/epitope for the group of peptides/epitopes tested. Non-natural (or modified) T-cell epitopes can further optionally be tested for their binding affinity to MHC class II molecules. The binding of non-natural (or modified) T-cell epitopes to MHC class II molecules can be performed in different ways. For instance, soluble HLA class II molecules are obtained by lysis of cells homozygous for a given class II molecule. The latter is purified by affinity chromatography. Soluble class II molecules are incubated with a biotin-labelled reference peptide produced according to its strong binding affinity for that class II molecule. Peptides to be assessed for class II binding are then incubated at different concentrations and their capacity to displace the reference peptide from its class II binding is calculated by addition of neutravidin. Methods can be found in for instance Texier et al., (2000) *J. Immunology* 164, 3177-3184).

The immunogenic peptides of the invention have a mean T cell stimulation index of greater than or equal to 2.0. An immunogenic peptide having a T cell stimulation index of greater than or equal to 2.0 is considered useful as a prophylactic or therapeutic agent. More particularly, immunogenic peptides according to the invention have a mean T cell stimulation index of at least 2.5, at least 3.5, at least 4.0, or even at least 5.0. In addition, such peptides typically have a positivity index (P.I.) of at least about 100, at least 150, at least about 200 or at least about 250. The positivity index for a peptide is determined by multiplying the mean T cell stimulation index by the percent of individuals, in a population of individuals sensitive to an alloantigen (e.g., at least 9 individuals, at least 16 individuals or at least 29 or 30, or even more), who have T cells that respond to the peptide (thus corresponding to the SI multiplied by the promiscuous nature of the peptide/epitope). Thus, the positivity index represents both the strength of a T cell response to a peptide (S.I.) and the frequency of a T cell response to a peptide in a population of individuals sensitive to an alloantigen. In order to determine optimal T cell epitopes by, for example, fine mapping techniques, a peptide having T cell stimulating activity and thus comprising at least one T cell epitope as determined by T cell biology techniques is modified by addition or deletion of amino acid residues at either the N- or C-terminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically. T cell epitopes or peptides are selected based on various factors, including the strength of the T cell response to the peptide/epitope (e.g., stimulation index) and the frequency of the T cell response to the peptide in a population of individuals.

Methods used for the identification of minor histocompatibility antigens are known in the art. Thus, positional cloning or expression cloning strategies can be used to identify candidate minor histocompatibility antigens. For full description of the methodology, see for instance Mendoza et al, Immunity, 7: 461-472, 1997. Alternatively, peptides actually presented by APC in either MHC class I or class II molecules can be eluted and separated by various chromatography methods. Full description of such methodology will be found in Scott et al, Immunity, 12: 711-720, 2000.

Candidate antigens can be screened by one or more in vitro algorithms to identify a T cell epitope sequence within an antigenic protein. Suitable algorithms include, but are not limited to those found on the following websites:
http://antigen.i2r.a-star.edu.sg/predBalbc/;
http://antigen.i2.r.a-star.edu.sg/predBalbc/;
http://www.imtech.res.in/raghava/mhcbn/;
http://www.syfpeithi.de/home.htm;
http://www-bs.informatik.uni-tuebingen.de/SVMHC;
http://bio.dfci.harvard.edu/Tools/antigenic.html;
http://www.jenner.ac.uk/MHCPred/.

More particularly, such algorithms allow the prediction within an antigenic protein of one or more nonapeptide sequences which will fit into the groove of an MHC II molecule.

The immunogenic peptides of the invention can be produced by recombinant expression in, e.g., bacterial cells (e.g. *Escherichia coli*), yeast cells (e.g., *Pichia* species, *Hansenula* species, *Saccharomyces* or *Schizosaccharomyces* species), insect cells (e.g. from *Spodoptera frugiperda* or *Trichoplusia ni*), plant cells or mammalian cells (e.g., CHO, COS cells). The construction of the therefore required suitable expression vectors (including further information such as promoter and termination sequences) involves meanwhile standard recombinant DNA techniques. Recombinantly produced immunogenic peptides of the invention can be derived from a larger precursor protein, e.g., via enzymatic cleavage of enzyme cleavage sites inserted adjacent to the N- and/or C-terminus of the immunogenic peptide, followed by suitable purification.

In view of the limited length of the immunogenic peptides of the invention, they can be prepared by chemical peptide synthesis, wherein peptides are prepared by coupling the different amino acids to each other. Chemical synthesis is particularly suitable for the inclusion of e.g. D-amino acids, amino acids with non-naturally occurring side chains or natural amino acids with modified side chains such as methylated cysteine. Chemical peptide synthesis methods are well described and peptides can be ordered from companies such as Applied Biosystems and other companies. Peptide synthesis can be performed as either solid phase peptide synthesis (SPPS) or contrary to solution phase peptide synthesis. The best-known SPPS methods are t-Boc and Fmoc solid phase chemistry which is amply known to the skilled person. In addition, peptides can be linked to each other to form longer peptides using a ligation strategy (chemoselective coupling of two unprotected peptide fragments) as originally described by Kent (Schnolzer & Kent (1992) *Int. J Pept. Protein Res.* 40, 180-193) and reviewed for example in Tam et al. (2001) *Biopolymers* 60, 194-205. This provides the tremendous potential to achieve protein synthesis which is beyond the scope of SPPS. Many proteins with the size of 100-300 residues have been synthesized successfully by this method. Synthetic peptides have continued to play an ever-increasing crucial role in the research fields of biochemistry, pharmacology, neurobiology, enzymology and molecular biology because of the enormous advances in the SPPS.

The physical and chemical properties of an immunogenic peptide of interest (e.g. solubility, stability) is examined to determine whether the peptide is/would be suitable for use in therapeutic compositions. Typically this is optimized by adjusting the sequence of the peptide. Optionally, the peptide can be modified after synthesis (chemical modifications e.g. adding/deleting functional groups) using techniques known in the art.

Accordingly, in yet a further aspect, the present invention provides methods for generating allograft antigen-specific cytotoxic T cells (Tregs or CD4+ regulatory T-cells) either in vivo or in vitro (ex-vivo). In particular T cells are provided which are cytotoxic towards any cell presenting an allograft antigen and are obtainable as a cell population. The invention accordingly extends to (populations of) allograft antigen-specific cytotoxic Tregs obtainable by the herein described methods.

In particular embodiments, methods are provided which comprise the isolation of peripheral blood cells, the stimulation of the cell population in vitro by contacting an immunogenic peptide according to the invention (i.e. comprising a T-cell epitope derived from an allogantigenic protein) with the isolated peripheral blood cells, and the expansion of the stimulated cell population, more particularly in the presence of IL-2. The methods according to the invention have the advantage that higher numbers of Tregs are produced and that the Tregs can be generated which are specific for the allograft antigenic protein (by using a peptide comprising an antigen-specific epitope). Alternatively, allograft antigenic protein-specific cytotoxic T cells may be obtained by incubation in the presence of APCs presenting an allograft antigenic protein-specific immunogenic peptide according to the invention after transduction or transfection of the APCs with a genetic construct capable of driving expression of such immunogenic peptide. Such APCs may in fact themselves be administered to a subject in need to trigger in vivo in said subject the induction of the beneficial subset of cytotoxic CD4+ T-cells.

In an alternative embodiment, the Tregs can be generated in vivo, i.e. by the administration of an immunogenic peptide provided herein to a subject, and collection of the Tregs generated in vivo.

The allograft antigen-specific regulatory T cells obtainable by the above methods are of particular interest for use in (the manufacture of a medicament for) preventing or treating in a recipient the rejection of an allograft. For any of the above-described uses of the immunogenic peptides of the invention, said peptides can be replaced by allograft antigen-specific Tregs. Both the use of allogeneic and autogeneic cells is envisaged. Any method comprising the administration of allograft antigen-specific Tregs to a subject in need (i.e., for preventing or treating allograft rejection) is also referred to in the art as "adoptive cell therapy". Such therapy is of particular interest in case of treating chronic allo graft-specific immune reactions and relapses of such reactions. Tregs are crucial in immunoregulation and have great therapeutic potential. The efficacy of Treg-based immunotherapy depends on the Ag specificity of the regulatory T cells. Moreover, the use of Ag-specific Treg as opposed to polyclonal expanded Treg reduces the total number of Treg necessary for therapy.

A further aspect of the present invention relates to nucleic acid sequences encoding the immunogenic peptides of the present invention and methods for their use, e.g., for recombinant expression or in gene therapy. In particular, said nucleic acid sequences are capable of expressing an immunogenic peptides of the invention.

The immunogenic peptides of the invention may indeed be administered to a subject in need by using any suitable gene therapy method. In any use or method of the invention for the treatment and/or prevention of allograft rejection, immunization with an immunogenic peptide of the invention may be combined with adoptive cell transfer of (a population of) Tregs specific for said immunogenic peptide and/or with gene therapy. When combined, said immunization, adoptive cell transfer and gene therapy can be used concurrently, or sequentially in any possible combination.

In gene therapy, recombinant nucleic acid molecules encoding the immunogenic peptides can be used as naked DNA or in liposomes or other lipid systems for delivery to target cells. Other methods for the direct transfer of plasmid DNA into cells are well known to those skilled in the art for use in human gene therapy and involve targeting the DNA to receptors on cells by complexing the plasmid DNA to proteins. In its simplest form, gene transfer can be performed by simply injecting minute amounts of DNA into the nucleus of a cell, through a process of microinjection. Once recombinant genes are introduced into a cell, they can be recognized by the cell's normal mechanisms for transcription and translation, and a gene product will be expressed. Other methods have also been described for introducing DNA into larger numbers of cells. These methods include: transfection, wherein DNA is precipitated with calcium phosphate and taken into cells by pinocytosis; electroporation, wherein cells are exposed to large voltage pulses to introduce holes into the membrane); lipofection/liposome fusion, wherein DNA is packed into lipophilic vesicles which fuse with a target cell; and particle bombardment using DNA bound to small projectiles. Another method for introducing DNA into cells is to couple the DNA to chemically modified proteins. Adenovirus proteins are capable of destabilizing endosomes and enhancing the uptake of DNA into cells. Mixing adenovirus to solutions containing DNA complexes, or the binding of DNA to polylysine covalently attached to adenovirus using protein crosslinking agents substantially improves the uptake and expression of the recombinant gene. Adeno-associated virus vectors may also be used for gene delivery into vascular cells. As used herein, "gene transfer" means the process of introducing a foreign nucleic acid molecule into a cell, which is commonly performed to enable the expression of a particular product encoded by the gene. The said product may include a protein, polypeptide, anti-sense DNA or RNA, or enzymatically active RNA. Gene transfer can be performed in cultured cells or by direct administration into mammals. In another embodiment, a vector comprising a nucleic acid molecule sequence encoding an immunogenic peptide according to the invention is provided. In particular embodiments, the vector is generated such that the nucleic acid molecule sequence is expressed only in a specific tissue. Methods of achieving tissue-specific gene expression are well known in the art, e.g., by placing the sequence encoding an immunogenic peptide of the invention under control of a promoter, which directs expression of the peptide specifically in one or more tissue(s) or organ(s). Expression vectors derived from viruses such as retroviruses, vaccinia virus, adenovirus, adeno-associated virus, herpes viruses, RNA viruses or bovine papilloma virus, may be used for delivery of nucleotide sequences (e.g., cDNA) encoding peptides, homologues or derivatives thereof according to the invention into the targeted tissues or cell population. Methods which are well known to those skilled in the art can be used to construct recombinant viral vectors containing such coding sequences. Alternatively, engineered cells containing a nucleic acid molecule coding for an immunogenic peptide according to the invention may be used in gene therapy.

Where the administration of one or more peptides according to the invention is ensured through gene transfer (i.e. the administration of a nucleic acid which ensures expression of peptides according to the invention in vivo upon administration), the appropriate dosage of the nucleic acid can be determined based on the amount of peptide expressed as a result of the introduced nucleic acid.

According to the present invention medicaments are envisaged for use in the treatment and/or prevention of allograft rejection. The medicament of the invention is usually, but not necessarily, a (pharmaceutical) formulation comprising as active ingredient at least one of the immunogenic peptides of the invention, a (population of) Tregs specific for said immunogenic peptide or a gene therapeutic vector capable of expressing said immunogenic peptide. Apart from the active ingredient(s), such formulation will comprise at least one of a (pharmaceutically acceptable) diluent, carrier or adjuvant. Typically, pharmaceutically acceptable compounds (such as diluents, carriers and adjuvants) can be found in, e.g., a Pharmacopeia handbook (e.g. US-, European- or International Pharmacopeia). The medicament or pharmaceutical composition of the invention normally comprises a (prophylactically or therapeutically) effective amount of the active ingredient(s) wherein the effectiveness is relative to the condition or disorder to be prevented or treated. In particular, the pharmaceutical compositions of the invention are vaccines for prophylactic or therapeutic application.

The medicament or pharmaceutical composition of the invention may need to be administered to a subject in need as part of a prophylactic or therapeutic regimen comprising multiple administrations of said medicament or composition. Said multiple administrations usually occur sequentially and the time-interval between two administrations can vary and will be adjusted to the nature of the active ingredient and the nature of the condition to be prevented or treated. The amount of active ingredient given to a subject in need in a single administration can also vary and will depend on factors such as the physical status of the subject (e.g. weight, age), the status of the condition to be prevented or treated, and the experience of the treating doctor, physician or nurse.

The term "diluents" refers for instance to physiological saline solutions. The term "adjuvant" usually refers to a pharmacological or immunological agent that modifies (preferably increases) the effect of other agents (e.g., drugs, vaccines) while having few if any direct effects when given by themselves. As one example of an adjuvant aluminium hydroxide (alum) is given, to which an immunogenic peptide of the invention can be adsorbed. Further, many other adjuvants are known in the art and can be used provided they facilitate peptide presentation in MHC-class II presentation and T cell activation. The term "pharmaceutically acceptable carrier" means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the active ingredient in the composition. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Suitable pharmaceutical carriers for use in said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 urn, namely for the manufacture of microcapsules for controlled or sustained release of the active ingredients.

Immunogenic peptides, homologues or derivatives thereof according to the invention (and their physiologically acceptable salts or pharmaceutical compositions all included in the term "active ingredients") may be administered by any route appropriate to the condition to be prevented or treated and appropriate for the compounds, here the immunogenic proteins to be administered. Possible routes include regional, systemic, oral (solid form or inhalation), rectal, nasal, topical (including ocular, buccal and sublingual), vaginal and parenteral (including subcutaneous, intramuscular, intravenous, intradermal, intraarterial, intrathecal and epidural). The preferred route of administration may vary with for example the condition of the recipient or with the condition to be prevented or treated.

The formulations may conveniently be presented in unit dosage form and may be prepared by any of the methods well known in the art of pharmacy. Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

A further aspect of the present invention provides isolated immunopeptides comprising a T-cell epitope from an MCH, a minor histocompatibility antigen or an tissue-specific antigen and C-(X)2-[CST] or [CST]-(X)2-C motif, the motif being adjacent to the T-cell epitope or separated from the T-cell epitope by a linker, most particularly a linker of at most 7 amino acids. In further particular embodiments the T-cell epitope is derived from a protein which is an established alloantigen. In particular embodiments, the T-cell epitope is from an MCH, minor histocompatibility antigen or tissue specific antigen wherein the motif does not naturally occur within a region of 11 amino acids N or C-terminally of the T-cell epitope.

In all of the methods and applications described herein, a particular allograft antigen is exemplified by the Dby antigen encoded by the H—Y chromosome. Therefore, the invention also relates to an immunogenic peptide comprising a T-cell epitope of the Dby antigen and, adjacent to said T-cell epitope or separated from said T-cell epitope by a linker, a C-(X)2-[CST] or [CST]-(X)2-C motif. In particular the T-cell epitope is characterized by FNSNRANSS (SEQ ID. NO: 5) or CHGCFNSNRANSS (SEQ ID NO:6), and exemplary immunogenic peptides of the invention comprising them are characterized by LVLAPTREL (SEQ ID. NO: 7) or CGHCLVLAPTREL (SEQ ID NO: 8). The invention further relates to herein described uses of/methods of using these immunogenic peptides as well as to herein described compositions/medicaments based on these immunogenic peptides.

The present invention will now be illustrated by means of the following examples, which are provided without any limiting intention. Furthermore, all references described herein are explicitly included herein by reference.

EXAMPLES

Example 1

Elicitation of Cytotoxic Regulatory T Cells by Immunization with a Modified Peptide The sequence of the murine Dby antigen, which is encoded by the H—Y chromosome, was entered into algorithms used to identify T cell epitopes for mice of the C57B1/6 strain. A putative epitope of sequence FNSNRANSS (SEQ ID. NO: 5) was identified and used as a backbone for the production of an immunogenic peptide according to the present invention, which includes a consensus sequence encompassing a thioreductase activity, namely CHGC (SEQ ID. NO: 9). A new peptide was therefore synthesized with sequence CHGCFNSNRANSS (SEQ ID. NO: 6; thioreductase consensus sequence underlined).

Groups of C57BL/6 female mice were immunized with 10 μg of peptide of SEQ ID. NO: 6 emulsified in CFA (complete Freund's adjuvant) for the first SC (subcutaneous) injection and in IFA (incomplete Freund's adjuvant) for the two subsequent immunizations. The spleen of such mice was retrieved 10 days after the last immunization and CD4+ T cells were obtained by cell sorting using magnetic beads.

These CD4+ T cells were assayed in vitro for their capacity to induce apoptosis of APC (antigen-presenting cells). Thus, spleen cells of naïve C57B1/6 mice were deprived of CD4+ T cells by magnetic bead sorting and used as APC. Such APC were loaded with peptides of either SEQ ID. NO: 5 or of SEQ ID. NO: 6 by incubation for 16 h at room temperature. The cells were then washed to eliminate residual free peptides.

Upon addition of CD4+ T cells obtained from mice immunized with the modified peptide, APC loaded with either the natural sequence (SEQ ID. NO: 5) or its modified counterpart (SEQ ID. NO: 6) were induced into apoptosis as seen by surface binding of Annexin V. Control CD4+ T cells, either from mice immunized with a sham antigen, or from mice immunized with the natural peptide of SEQ ID. NO: 5 did not induce any significant degree of APC apoptosis.

These experiments demonstrate that a T cell epitope of a minor histocompatibility antigen can, by direct immunization in the mouse and after modification according to the present invention by addition of a thioreductase moiety, elicit cytotoxic Tregs. It further demonstrates that cytotoxic Tregs can be activated and exert their immunosuppressive properties when activated by the natural sequence of the T epitope. Altogether, this provides evidence that cytotoxic Tregs specific of minor histocompatibility antigens can be generated by direct immunization.

Example 2

Preclinical Model for the Prevention of Graft Rejection (Naïve Mice)

One of the most studied models of graft rejection is skin grafting between syngeneic animals of different sex. Thus, the H-Y chromosome contains a number of genes, in particular the Dby gene, which encodes a minor histocompatibility antigen that elicits strong CD4+ T cell activation and chronic rejection in females. It has been demonstrated that rejection is primarily due to presentation of the Dby antigen by female APCs, namely through the indirect pathway (see Braun et al, Journal of Immunology, 166: 4879-4883, 2001).

This model is considered to be directly relevant to the human situation, because H-Y derived antigens are also expressed in man. Besides, it is known that bone marrow or solid organ grafts from male donors are more frequently rejected by female recipients than when the graft is of female origin.

T cell epitopes from the Dby antigen have been described and selected as shown in Example 1 (peptide of SEQ ID. NO: 5). A synthetic peptide of SEQ ID. NO: 6 was prepared. Groups of 3 female C57Bl/6 mice (H-2b haplotype) were made for testing the capacity of modified peptides of SEQ ID NO:1 to elicit tolerance to the skin allograft. Where applicable, pre-immunization was carried out by 3 subcutaneous injections of peptides containing either the natural epitope or its modified counterpart. Injections were made at fortnight intervals in either CFA/IFA or alum. Groups were therefore as follows:

Group 1: skin allograft without preimmunization
Group 2: skin autograft
Group 3: preimmunization with peptide of SEQ ID. NO: 6 emulsified in CFA (first immunization) and IFA for second and third immunization)
Group 4: same as in Group 3, but with alum as an adjuvant
Group 5: same as in Group 3, but using the natural peptide of SEQ ID. NO: 5

All these mice, except for Group 2 mice, received a male C57Bl/6 skin allograft of 1 cm2, either directly (Group 1) or 2 weeks after the last immunization for Groups 3, 4 and 5. Group 2 mice received and autograft. Rejection rate was evaluated at day 10 and 20 and judged effective if more than 50% of the graft surface was necrotic. Table 1 summarizes the results.

TABLE 1

Summary of the rejection rate of an experiment in which female C57Bl/6 mice grafted with skin from syngeneic males are rendered tolerant to the allograft by pre-immunization with a peptide containing a CD4+ T cell epitope linked to a thioreductase consensus sequence.

| Groups of 3 mice unless indicated | Day 10 | Day 20 |
|---|---|---|
| Group 1 allograft | 3/3 | 2/3* |
| Group 2 autograft (n = 6) | 1/6 | 1/6 |
| Group 3 pre-immunization in CFA/IFA with SEQ ID. NO: 6 | 0/3 | 0/3 |
| Group 4 pre-immunization in alum with SEQ ID. NO: 6 | 0/3 | 0/3 |
| Group 5 pre-immunization with SEQ ID. NO: 5 | 2/3 | 2/3** |

*1 accidental death
**accelerated rejection process

These experiments indicate that pre-immunization with modified peptide of SEQ ID. NO: 6 in either CFA/IFA or alum fully prevents graft rejection, whilst pre-sensitization with natural peptide of SEQ ID. NO: 5 accelerates the rejection.

These experiments were carried out using wildtype C57Bl/6 female mice, which carry a repertoire of T cells of the CD4+ lineage that can be activated by all MHC class II-restricted T cell epitopes derived from the H-Y chromosome. Besides, such mice have a normal CD8+ T cell repertoire, which can be activated by MHC class I-restricted T cell epitopes. As it is known that cytotoxic CD8+ T cells are sufficient to reject graft, we can conclude that a modified peptide of SEQ ID. NO: 6 not only prevent rejection via activation of CD4+ T cells, but also suppresses rejection via CD8+ T cells.

H-Y antigens are also present in man, where they play the role of minor histocompatibility antigens, much alike in the mouse. The Dby antigen is recognized as one of the main of such antigens. The sequence of one of the main T cell epitope of human Dby is LVLAPTREL (SEQ ID. NO: 7). This T-cell epitope can be modified according to the present invention by addition of a consensus sequence containing a thioreductase activity, for example resulting in an immunogenic peptide CGHCLVLAPTREL (SEQ ID. NO: 8).

Example 3

Preclinical Model for the Prevention of Graft Rejection (Primed Mice)

The above experiments were carried out in naïve mice directly immunized with a peptide modified according to the present invention. As in the clinic patients waiting for a graft are often already sensitized towards alloantigens, due for instance to previous blood infusion or pregnancy, an experiment was designed to evaluate the effect of modified peptides administered to mice already sensitized to the Dby antigen.

Thus, groups of C57Bl/6 female mice are adoptively transferred with splenocytes from syngeneic male mice. This is carried out by injecting $20.10^6$ cells either intraperitoneally or subcutaneously. Ten days after, the spleen of such mice is retrieved to confirm that CD4+ effector T cells are generated towards the Dby antigen.

Mice presensitized by adoptive transfer of cells are then grafted with male skin as described in Example 2. Tolerance to skin grafting in such pre-immunized mice is subsequently assessed.

These experiments demonstrate that in vivo administration of an immunogenic peptide of the invention eliminates or neutralizes the function of existing effector CD4+ T cells to the Dby antigen.

Example 4

Cytotoxic Tregs Specific for the Dby Antigen Suppress the Capacity of CD4+ Effector Cells to Activate CD8+ Cytolytic T Cells to the Uty Antigen and Thereby Prevent CD8+-Mediated Graft Rejection Mata-Hari mice are Rag1−/− mice that express a T cell receptor recognizing a class I restricted H2b epitope of the Uty antigen, an alternative antigen encoded by the H-Y chromosome. Such mice can reject skin graft from syngeneic male H2b mice through CD8+ T cell activation.

CD8+ transgenic T cells from Mata-Hari mice are used to adoptively reconstitute H2b Rag2−/− mice using a number of cells that is sufficient to mediate rejection only when help is provided by effector CD4+ T cells.

In order to provide such help, effector CD4+ T cells as well as cytotoxic CD4+ regulatory T cells are prepared in naïve H2k mice by immunization with the corresponding peptides of SEQ ID NOs: 5 and 6, respectively, as described in Example 1.

Effector or cytotoxic H2k-restricted CD4+ T cells are transferred into Rag2−/− mice already reconstituted with transgenic H2b-restricted CD8+ T cells. In order to ensure that CD4+ T cells, either effectors or cytotoxic T cells are activated in vivo, Rag2−/− mice also receive a transplant of H2k splenocytes from a male mouse.

Reconstituted Rag2−/− mice are then grafted with the skin of an H2b male and the rejection of the graft is followed over 3 weeks. In such a system, the limiting number of CD8+ T cells will reject the H2b graft only if they receive help from effector CD4+ T cells, which are activated by H2k restricted splenocytes, so as to avoid graft rejection by effector T cells.

Co-reconstitution with CD4+ effector and CD4+ cytotoxic cells abolishes the capacity of effector CD4+ T cells to provide help for CD8+-mediated graft rejection.

Injection of Cytotoxic CD4+ T cells recognizing an MHC-class II peptide of one antigen (Dby) down-regulate the CD8+-mediated graft rejection through recognition of another antigen (Uty) encoded by the H-Y chromosome.

Example 5

Rejection of Graft Caused by Divergent MHC Class II Antigens is Prevented by Cytotoxic CD4+ Regulatory T Cells The Bm12 mice constitute a variant of the C57B1/6 mice in which a spontaneous mutation has occurred in the I-Ab locus. This mutation consists of 3 amino acid substitutions in a stretch of 5 amino acids and thereby generates a limited MHC class II mismatch between Bm12 mice and C57B1/6 wild type mice. This mismatch is nevertheless sufficient as to elicit rejection of Bm12 mouse skin allograft.

The 3 substituted amino acids are Ile67Phe, Arg70Gln and Thr71Lys located in the third hypervariable region of the beta chain. A synthetic peptide encompassing these residues was made and has the sequence: PEFLEQKRA (SEQ ID. NO: 10). This peptide was modified according to the invention by incorporation of a thioreductase consensus sequence, resulting in the exemplary immunogenic peptide CGHCPEFLEQKRA (SEQ ID. NO: 11).

Cytotoxic CD4+ regulatory T cells towards the modified peptide of SEQ ID. NO: 11 are elicited in C57B1/6 mice by 3 subcutaneous administration of the peptide in CFA/IFA given at fortnight intervals. Such mice are then grafted with the skin of Bm12 mice.

It is observed that C57B1/6 mice rapidly reject the B12m graft unless they are preimmunized with the peptide of SEQ ID. NO: 11, but not when the natural peptide of SEQ ID. NO: 10 is used for preimmunization. These experiments demonstrate that immunogenic peptides of the invention can elicit CD4+ cytotoxic regulatory T cells and thereby allow tolerance of an allograft with MHC class II mismatch.

Example 6

Cytotoxic Regulatory CD4+ T Cells are Elicited by In Vivo Immunization with a Peptide Comprising a Minor Histocompatibility Antigen HA-1 T Cell Epitope to which a Thioreductase Consensus Sequence is Added BALB/c mice (group 1) are immunized with 25 µg of a peptide containing a (natural) T-cell epitope of HA-1 minor histocompatibility antigen by 3 footpath injections in CFA/IFA made at a fortnight interval. The sequence of the peptide corresponds to amino acids 302 to 310 of HA-1, namely: ARLQVAKAE (SEQ ID NO:12)

A second group of BALB/c mice (group 2) are immunized using the same protocol with peptide of SEQ ID NO: 12 to which a consensus motif exhibiting thioreductase activity (or shortly: redox motif) is added at the amino-terminal end, resulting in CHGCARLQVAKAE (SEQ ID NO: 13; redox motif underlined) referred to as the modified T-cell epitope).

Ten days after the last immunization, the spleens of all mice are recovered and CD4+ T cells are prepared by sorting on magnetic beads.

Spleen adherent cells prepared from naïve BALB/c mice are used as antigen-presenting cells (APC). Such APC ($2 \times 10^7$) are loaded with either peptide of SEQ ID NO: 12 or peptide of SEQ ID NO: 13 (5 µg/mL) by an 1-h incubation followed by a wash.

CD4+ T cells obtained from either group 1 or group 2 mice are added to the population of APCs and co-cultured for 24 h at 37° C. Cells are then recovered and incubated with a fluorescent-labelled anti-CD11c antibody and with FITC-labelled annexin V as a marker of apoptosis. Finally, cells are analyzed by Facs analysis.

These experiments demonstrate that a peptide of SEQ ID NO: 13 can elicit CD4+ T cells with cytotoxic properties towards APCs presenting either the natural HA-1 minor histocompatibility antigen T-cell epitope (SEQ ID NO:12) or the modified HA-1 minor histocompatibility antigen T-cell epitope (SEQ ID NO:13).

Example 7

Preclinical Model for the Prevention of Graft Rejection of Vascularized Organs (Naïve Mice)

The Dby gene product as described in Example 2 is presented by both MHC class I and MHC class II determinants. In grafting vascularized organs such as the heart, in addition to MHC class I presentation, cells from the endothelium can express MHC class II molecules as well as co-stimulatory molecules such as B7. This provides endothelial cells with the capacity to activate both CD8+ and CD4+ T cells specific for alloantigens in the context of MHC class I or class II, respectively.

However, CD4+ T cells play a major role in graft rejection, as depletion of CD4+ T cells, but not of CD8+ T cells from the recipient completely prevents rejection (Szeto W Y et al, Transplantation (2002) 73: 1116-1122). Besides, the production by effector CD4+ T cells of pro-inflammatory cytokines enhances local inflammation, mostly at the level of the graft endothelium, which results in increased endothelitis with increased MHC determinants expression. Therefore, a method by which such alloantigen-specific CD4+ T cells are eliminated would allow induction of tolerance to the graft.

It is known in the art that the indirect pathway of alloantigen recognition is predominant, namely the presentation by recipient's APC of antigens shed by the graft to recipient's CD4+ T cells. Therefore, preventing the expansion and activation of effector CD4+ T cells by the indirect pathway would be much desirable.

To establish the proof of concept that cytolytic regulatory CD4+ T cells of the present invention can prevent rejection of a vascularized organ, the model of heterotopic heart transplantation is used. This method is well known in the art, as described for instance in Kadner A et al, European Journal of Cardio-thoracic Surgery (2000) 17: 474-481. Briefly, the method consists in abdominal implantation of the heart in a non-working setting, namely the heart is vascularized but not supporting the circulation. This allows long-term follow-up of the graft and multiple biopsies without killing the experimental animal.

Hearts from C57BL/6 males are grafted using such technique in the abdomen of syngeneic females. The rejection process, which is mediated by expression of H-Y-derived antigens in both MHC class I and MHC class II determinants, is mainly due to the circulation of recipient's specific CD4+ T cells that are activated by recognition of alloantigen-derived peptides by graft endothelial cells. Such CD4+ T cells produce IL-2 and IFN-gamma, driving more inflammation and providing help for the maturation of specific CD8+ T cells.

C57B1/6 female mice are pre-immunized before receiving the male allograft with peptides of either SEQ ID NO:5, SEQ ID NO:6 or a sham peptide. This is carried out by 3 subcutaneous injections of peptides made at fortnight intervals in either CFA/IFA. Thereafter, all mice receive a heterotopic male heart transplant.

It is observed that female mice pre-immunized with peptide of SEQ ID NO:6 (namely the modified peptide of Dby containing the thioreductase motif) tolerate the graft, as illustrated by continuing beating, and the demonstration of absence of cellular infiltration, of signs of endothelitis and of chronic vascular lesions. By contrast, mice pre-immunized with sham peptide or with peptide of sequence SEQ ID NO:5 show rejection of the transplanted heart.

These experiments demonstrate that preventing the expansion of CD4+ and CD8+ T cells specific for the products encoded by the H-Y chromosome by the elicitation of cytolytic regulatory CD4+ T cells to one of the epitopes of the Dby alloantigen, according to the present invention, is sufficient to prevent rejection of vascularized organs.

The invention claimed is:

1. A method of suppressing an immune response against an allogeneic protein expressed by a mammalian solid organ allograft, comprising the steps of administering to a recipient, prior to or after introducing said allograft to said recipient, at least one isolated immunogenic peptide with a length of between 13 and 50 amino acids, said peptide comprising (i) an MHC class II restricted T-cell epitope of 9 amino acids of said allogeneic protein expressed by said allograft and comprising (ii) a C-(X)2-C redox motif, wherein X is not cysteine, and wherein said motif is adjacent to said T-cell epitope, or is separated from said T-cell epitope by a linker of at most 4 amino acids, wherein said administering generates a population of cytotoxic CD4+ T cells against antigen presenting cells presenting said allogeneic protein.

2. The method of claim 1, said immunogenic peptide suppressing activation of CD4+ effector T-cells of said recipient by an alloantigenic protein of said allograft.

3. The method of claim 1, said immunogenic peptide inducing in a recipient CD4+ regulatory T cells which are cytotoxic to cells presenting an alloantigenic protein of said allograft.

4. The method of claim 1, said immunogenic peptide suppressing activation of CD8+ effector T-cells of the recipient by an alloantigenic protein of said allograft.

5. The method according to claim 1 wherein said solid organ graft is a kidney, lung, heart, liver, pancreas, bone or skin.

6. The method according to claim 1, wherein said allogeneic protein is selected from the group of minor histocompatibility antigens, major histocompatibility antigens or tissue-specific antigens.

7. The method according to claim 1 wherein said motif does not naturally occur within a region of 11 amino acids N- or C-terminally adjacent to the T-cell epitope in said allogeneic protein.

8. The method according to claim 1 wherein said immunogenic peptide further comprises an endosomal targeting sequence.

9. The method according to claim 1 wherein said motif is positioned N-terminally of the T-cell epitope.

10. The method according to claim 1 wherein at least one X in said motif is Gly, Ala, Ser or Thr.

11. The method according to claim 1 wherein at least one X in said motif is His or Pro.

12. The method according to claim 1 wherein at least one C in said motif is methylated.

13. The method according to claim 1 wherein said immunogenic peptide is produced by chemical synthesis or by recombinant expression.

14. The method according to claim 1 wherein said allogeneic protein is the Dby antigen encoded by the H-Y chromosome.

15. The method according to claim 1, wherein the recipient is a human and said solid organ allograft is a human solid organ.

* * * * *

SEQUENCE LISTING

```
<160> NUMBER OF SEQ ID NOS: 17

<210> SEQ ID NO 1
<211> LENGTH: 14
<212> TYPE: PRT
<213> ORGANISM: Artificial Sequence
<220> FEATURE:
<223> OTHER INFORMATION: motif repeat
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (12)..(13)
<223> OTHER INFORMATION: Xaa can be any naturally occurring amino acid

<400> SEQUENCE: 1

Cys Xaa Xaa Cys Xaa Cys Xaa Xaa Cys Xaa Cys Xaa Xaa Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: motif repeat
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (10)..(11)
<223> OTHER INFORMATION: Xaa can be any naturally occurring amino acid

<400> SEQUENCE: 2

Cys Xaa Xaa Cys Cys Xaa Xaa Cys Cys Xaa Xaa Cys
1               5                   10

<210> SEQ ID NO 3
<211> LENGTH: 10
<212> TYPE: PRT
<213> ORGANISM: Artificial Sequence
<220> FEATURE:
```

```
<223> OTHER INFORMATION: motif repeat
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (5)..(6)
<223> OTHER INFORMATION: Xaa can be any naturally occurring amino acid
<220> FEATURE:
<221> NAME/KEY: MISC_FEATURE
<222> LOCATION: (8)..(9)
<223> OTHER INFORMATION: Xaa can be any naturally occurring amino acid

<400> SEQUENCE: 3

Cys Xaa Xaa Cys Xaa Xaa Cys Xaa Xaa Cys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: motif repeat
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid

<400> SEQUENCE: 4

Cys Xaa Cys Cys Xaa Cys Cys Xaa Cys Cys
1               5                   10

<210> SEQ ID NO 5
<211> LENGTH: 9
<212> TYPE: PRT
<213> ORGANISM: Artificial Sequence
<220> FEATURE:
<223> OTHER INFORMATION: T cell epitope of Dby antigen

<400> SEQUENCE: 5

Phe Asn Ser Asn Arg Ala Asn Ser Ser
1               5

<210> SEQ ID NO 6
<211> LENGTH: 13
<212> TYPE: PRT
<213> ORGANISM: Artificial Sequence
<220> FEATURE:
<223> OTHER INFORMATION: redox motif + T cell epitope of Dby antigen

<400> SEQUENCE: 6

Cys His Gly Cys Phe Asn Ser Asn Arg Ala Asn Ser Ser
1               5                   10

<210> SEQ ID NO 7
<211> LENGTH: 9
<212> TYPE: PRT
<213> ORGANISM: Artificial Sequence
<220> FEATURE:
<223> OTHER INFORMATION: T cell epitope of Dby antigen

<400> SEQUENCE: 7
```

```
Leu Val Leu Ala Pro Thr Arg Glu Leu
1               5

<210> SEQ ID NO 8
<211> LENGTH: 13
<212> TYPE: PRT
<213> ORGANISM: Artificial Sequence
<220> FEATURE:
<223> OTHER INFORMATION: redox motif + T cell epitope of Dby antigen

<400> SEQUENCE: 8

Cys Gly His Cys Leu Val Leu Ala Pro Thr Arg Glu Leu
1               5                   10

<210> SEQ ID NO 9
<211> LENGTH: 4
<212> TYPE: PRT
<213> ORGANISM: Artificial Sequence
<220> FEATURE:
<223> OTHER INFORMATION: redox motif

<400> SEQUENCE: 9

Cys His Gly Cys
1

<210> SEQ ID NO 10
<211> LENGTH: 9
<212> TYPE: PRT
<213> ORGANISM: Artificial Sequence
<220> FEATURE:
<223> OTHER INFORMATION: mutated sequence of I-Ab locus

<400> SEQUENCE: 10

Pro Glu Phe Leu Glu Gln Lys Arg Ala
1               5

<210> SEQ ID NO 11
<211> LENGTH: 13
<212> TYPE: PRT
<213> ORGANISM: Artificial Sequence
<220> FEATURE:
<223> OTHER INFORMATION: redox motif + mutated version of I-Ab locus

<400> SEQUENCE: 11

Cys Gly His Cys Pro Glu Phe Leu Glu Gln Lys Arg Ala
1               5                   10

<210> SEQ ID NO 12
<211> LENGTH: 9
<212> TYPE: PRT
<213> ORGANISM: Artificial Sequence
<220> FEATURE:
<223> OTHER INFORMATION: T cell epitope of HA-1 minor histocompatibility
      antigen

<400> SEQUENCE: 12

Ala Arg Leu Gln Val Ala Lys Ala Glu
1               5

<210> SEQ ID NO 13
<211> LENGTH: 13
<212> TYPE: PRT
<213> ORGANISM: Artificial Sequence
<220> FEATURE:
<223> OTHER INFORMATION: redox motif + T cell epitope of HA-1 minor
      histocompatibility antigen
```

```
<400> SEQUENCE: 13

Cys His Gly Cys Ala Arg Leu Gln Val Ala Lys Ala Glu
1               5                   10

<210> SEQ ID NO 14
<211> LENGTH: 5
<212> TYPE: PRT
<213> ORGANISM: Artificial Sequence
<220> FEATURE:
<223> OTHER INFORMATION: redox motif + linker sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: connected to epitope

<400> SEQUENCE: 14

Cys Xaa Xaa Cys Gly
1               5

<210> SEQ ID NO 15
<211> LENGTH: 6
<212> TYPE: PRT
<213> ORGANISM: Artificial Sequence
<220> FEATURE:
<223> OTHER INFORMATION: redox motif + linker sequence
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: connected to epitope

<400> SEQUENCE: 15

Cys Xaa Xaa Cys Gly Gly
1               5

<210> SEQ ID NO 16
<211> LENGTH: 7
<212> TYPE: PRT
<213> ORGANISM: Artificial Sequence
<220> FEATURE:
<223> OTHER INFORMATION: redox motif + linker sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: connected to epitope sequence
<220> FEATURE:
<221> NAME/KEY: MISC_FEATURE
<222> LOCATION: (7)..(7)
<223> OTHER INFORMATION: connected to epitope

<400> SEQUENCE: 16

Cys Xaa Xaa Cys Ser Ser Ser
1               5
```

```
<210> SEQ ID NO 17
<211> LENGTH: 8
<212> TYPE: PRT
<213> ORGANISM: Artificial Sequence
<220> FEATURE:
<223> OTHER INFORMATION: redox motif + linker sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(4)
<223> OTHER INFORMATION: Xaa can be any naturally occurring amino acid
      sequence
<220> FEATURE:
<221> NAME/KEY: MISC_FEATURE
<222> LOCATION: (8)..(8)
<223> OTHER INFORMATION: connected to epitope

<400> SEQUENCE: 17

Cys Xaa Xaa Cys Ser Gly Ser Gly
1               5
```